(12) United States Patent
D'Oracio De Almeida et al.

(10) Patent No.: US 10,508,861 B1
(45) Date of Patent: Dec. 17, 2019

(54) REFRACTORY ANCHOR DEVICE AND SYSTEM

(71) Applicant: BRAND SHARED SERVICES, LLC, Kennesaw, GA (US)

(72) Inventors: Eduardo Fernando D'Oracio De Almeida, League City, TX (US); Anthony Stephen Harris, Conroe, TX (US)

(73) Assignee: BRAND SHARED SERVICES, LLC, Kennesaw, GA (US)

(*) Notice: Subject to any disclaimer, the term of this patent is extended or adjusted under 35 U.S.C. 154(b) by 0 days.

(21) Appl. No.: 16/527,848

(22) Filed: Jul. 31, 2019

Related U.S. Application Data

(63) Continuation of application No. 16/526,564, filed on Jul. 30, 2019.
(60) Provisional application No. 62/715,894, filed on Aug. 8, 2018.

(51) Int. Cl.
  *F27D 1/14* (2006.01)
  *F23M 5/04* (2006.01)

(52) U.S. Cl.
  CPC .............. *F27D 1/142* (2013.01); *F23M 5/04* (2013.01)

(58) Field of Classification Search
  CPC .................................. F27D 1/142; F23M 5/04
  USPC ................. 52/378, 334, 443, 506.02, 747.13
  See application file for complete search history.

(56) References Cited

U.S. PATENT DOCUMENTS

| | | | |
|---|---|---|---|
| 1,945,925 A | 2/1934 | Stiefel | |
| 1,962,906 A * | 6/1934 | Mueller | E04H 12/28 52/564 |
| 1,974,279 A | 9/1934 | Jones | |
| 4,479,337 A | 10/1984 | Crowley | |
| 4,581,867 A | 4/1986 | Crowley | |
| 4,651,487 A * | 3/1987 | Nishikawa | F27D 1/141 110/336 |
| 4,660,343 A | 4/1987 | Raycher et al. | |
| 4,680,908 A | 7/1987 | Crowley | |

(Continued)

OTHER PUBLICATIONS

HexMesh (Hanlock-Causeway) 1.

(Continued)

*Primary Examiner* — Joshua K Ihezie
(74) *Attorney, Agent, or Firm* — Gardner Groff & Greenwald, PC

(57) ABSTRACT

Refractory anchoring devices include a main body and a mounting feature for mounting to a thermal vessel. The main body has the shape of two end-to-end Y's forming a central segment, two branch segments extending from each end of the central segment, and an extension segment extending from each of the four branch segments, to collectively form four unenclosed cell openings that are each semi-hexagonal in shape. Some embodiments include four reinforcement segments with each one extending into a respective cell opening, four voids with each one extending through respective adjacent branch and extension segments, an underbody gap formed under the central segment for refractory interlinking between cell openings, and/or a single stud-welding stud for the mounting feature. Refractory anchoring systems and methods include an array of the refractory anchoring devices arranged and mounted so that the unenclosed semi-hexagonal cell openings of adjacent anchoring devices cooperatively form substantially hexagonal cells.

18 Claims, 14 Drawing Sheets

(56) References Cited

U.S. PATENT DOCUMENTS

| | | | |
|---|---|---|---|
| 4,711,186 | A | 12/1987 | Chen et al. |
| 4,753,053 | A | 6/1988 | Heard |
| D375,892 | S | 11/1996 | Kraemer, Jr. et al. |
| D393,588 | S | 4/1998 | Tuthill |
| 6,393,789 | B1 * | 5/2002 | Lanclos ................. B04C 5/085 110/338 |
| 6,887,551 | B2 * | 5/2005 | Hyde ....................... B32B 3/12 428/99 |
| D559,672 | S | 1/2008 | Alexander |
| D576,479 | S | 9/2008 | Alexander |
| 8,656,679 | B1 | 2/2014 | Duhon |
| 9,127,890 | B2 | 9/2015 | Garot |
| 9,279,245 | B2 | 3/2016 | Garot |
| 9,861,949 | B2 * | 1/2018 | Simon ....................... B32B 3/12 |
| 10,352,619 | B2 * | 7/2019 | Yoder .................... B01J 19/02 |
| 2004/0226251 | A1 * | 11/2004 | Hyde ....................... E04C 5/04 52/674 |
| 2015/0147236 | A1 | 5/2015 | Simon et al. |
| 2015/0267122 | A1 * | 9/2015 | Hinson ................. C10G 9/005 208/131 |
| 2017/0321962 | A1 | 11/2017 | Decker et al. |
| 2018/0320973 | A1 | 11/2018 | Yoder et al. |
| 2018/0345401 | A1 | 12/2018 | Giaramita et al. |

OTHER PUBLICATIONS

HexMesh (Hanlock-Causeway)2.
HexMesh (RAI).
K-Bar hex anchors (drawing).
K-Bar hex anchors (Kraemer Gunite).
K-Bar hex anchors (RAI).

* cited by examiner

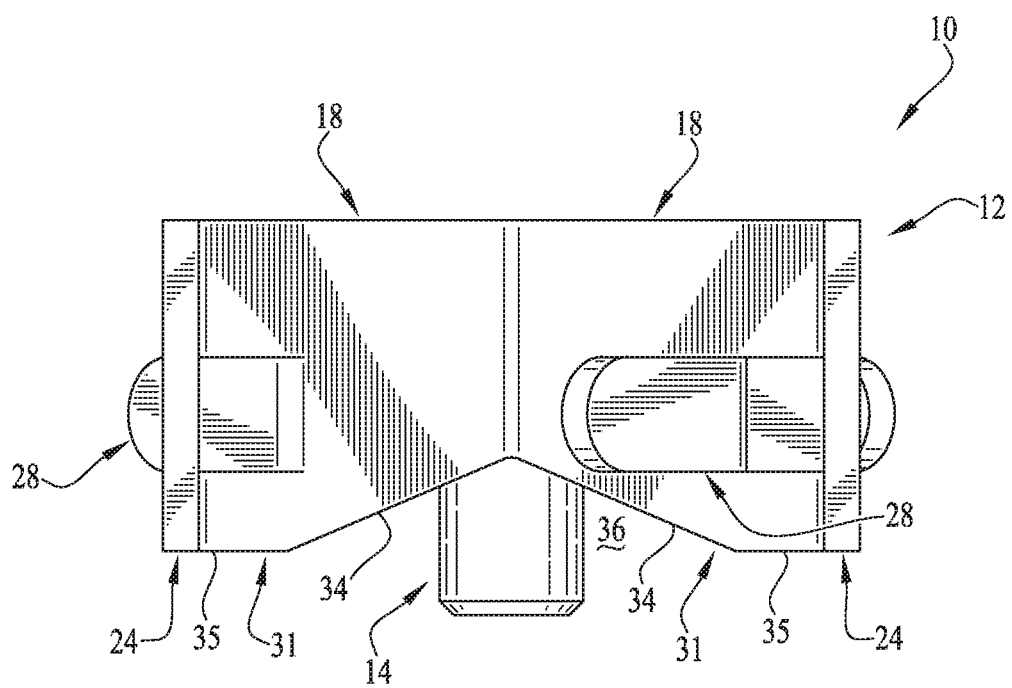

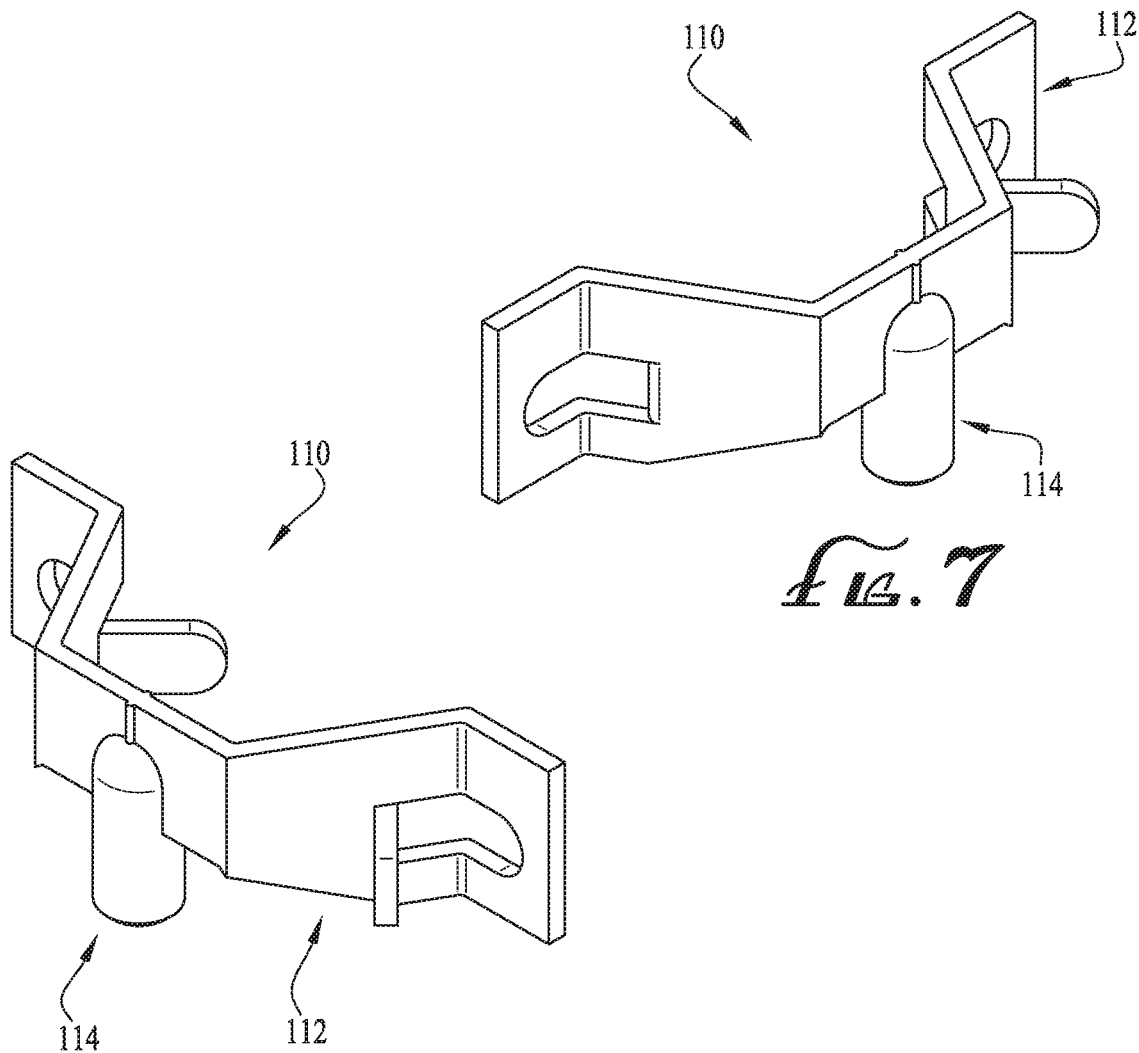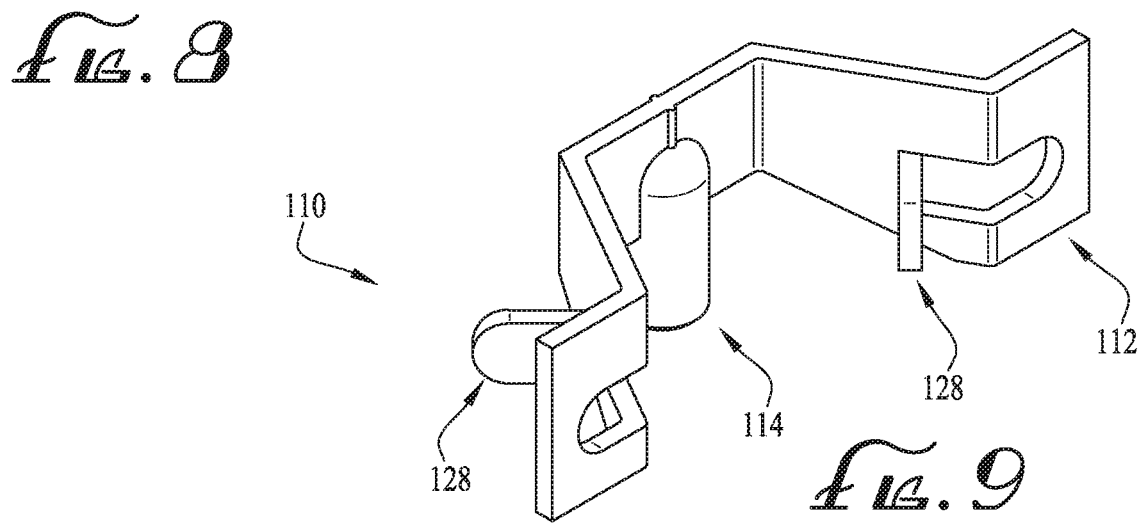

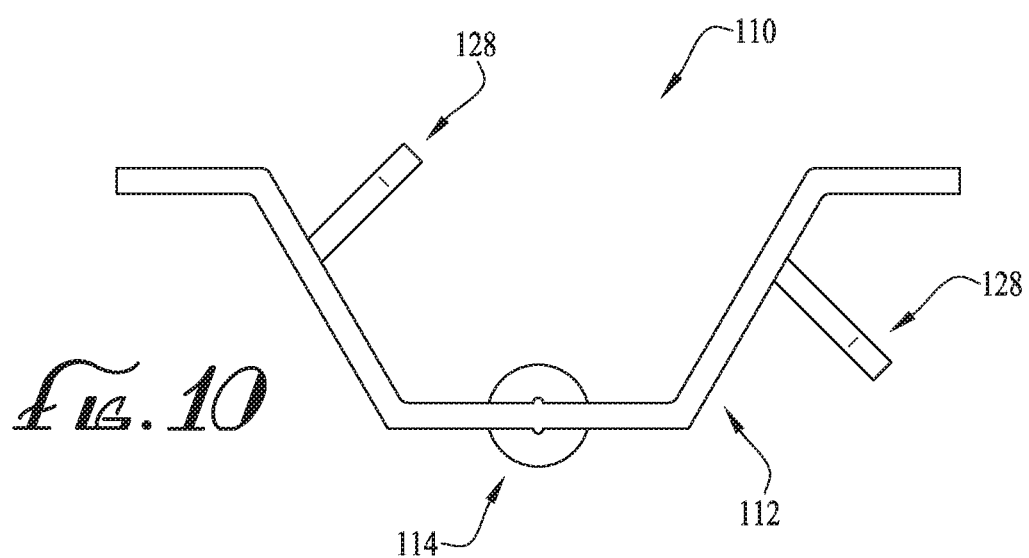
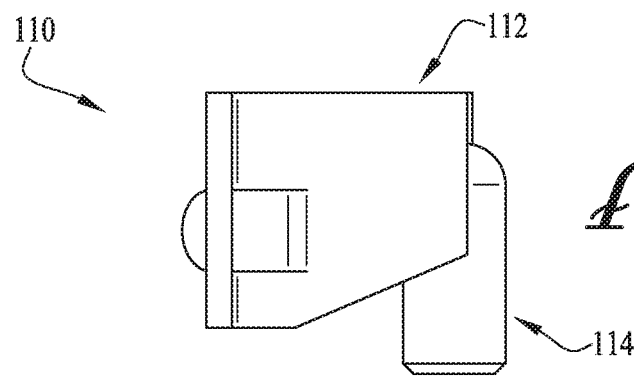
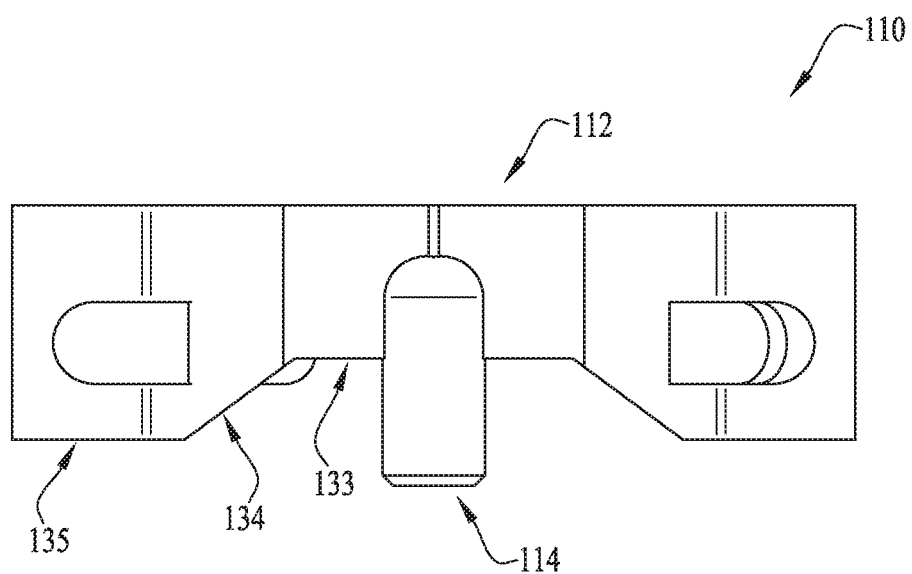

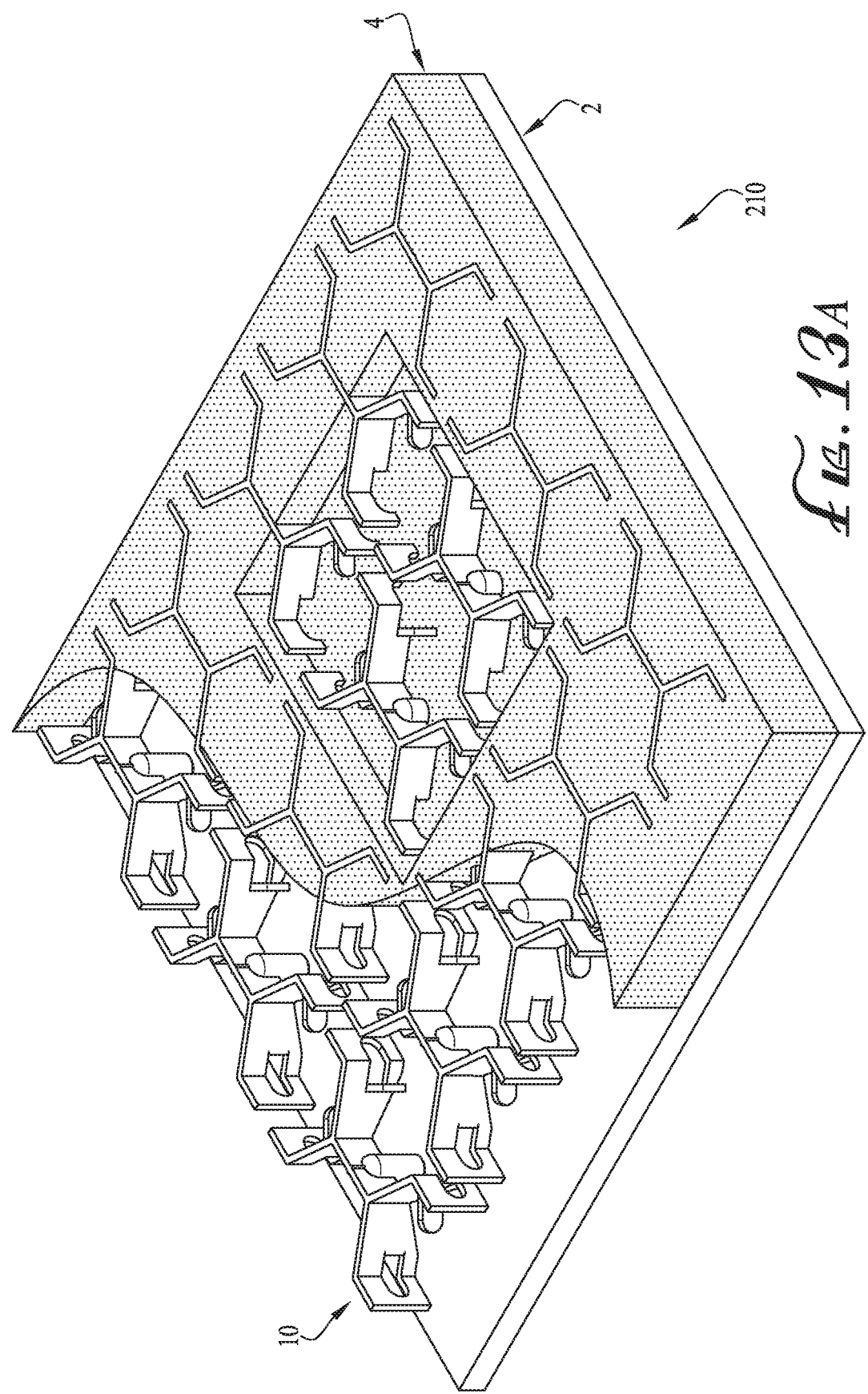

REFRACTORY ANCHOR DEVICE AND SYSTEM

CROSS-REFERENCE TO RELATED APPLICATIONS

This application is a continuation of U.S. Non-Provisional patent application Ser. No. 16/526,564 filed Jul. 30, 2019, which claims the priority benefit of U.S. Provisional Patent Application Ser. No. 62/715,894 filed Aug. 8, 2018, which are hereby incorporated herein by reference.

TECHNICAL FIELD

The present invention relates generally to the field of refractory linings for high-temperature vessels used in industrial and chemical processes, and more particularly to anchor systems for holding refractory materials in place in high-temperature and abrasive environments.

BACKGROUND

Thermal-process vessels used in oil refineries and other petrochemical and chemical process facilities have highly abrasive and high-temperature environments. To protect the vessel shells (e.g., sidewalls), their internal surface is typically lined with a refractory material such as a thin layer of concrete. To secure the refractory material in place, anchoring devices and systems have been developed.

The most common form of thin-layer abrasion-resistant refractory concrete anchoring system is called HEXMESH (aka "hexmetal" or just "hex") anchor sheets. Hex includes a series of steel strips that are interlocked (i.e., "clinched" together by a tab-and-slot arrangement) to form a sheet or mat of hexagonal cells in a honeycomb-patterned array or grid. The hex sheets are installed by fitting (bending/shaping and cutting/sizing) them to whatever vessel shape and size is to be lined, and then welding them in place by a large number of welds to create a strong attachment to the underlying vessel shell. Once welded, mixed refractory concrete is then rammed, beaten, or packed into the hex cells. The refractory concrete and hex sheet together form a barrier system that protects the underlying vessel shell from heat, abrasion, and chemical attack.

Over the decades that hex has been in use, several weaknesses in this system have been exposed. The hex and refractory system must move in concert with any flex that occurs in the vessel shell because the hex sheet is fitted and welded flush with and rigidly to the vessel shell. This makes the hex and refractory system prone to "biscuiting," which means individual hex cells will tend to "pop" the refractory concrete out in a hexagonal biscuit shape when the vessel shell experiences thermal expansion or contraction. In addition, this can compromise the protective capabilities of the refractory concrete liner by opening gaps that allow catalysts, gases, carbon, and other process-related materials to contact the exposed portion of the vessel shell. This in turn can lead to further failure of the refractory concrete liner system and the need for premature replacement of extremely expensive process vessels and components. Furthermore, installing hex is very time-consuming, tedious, and cumbersome because of the large number of welds required and because the sheets must be cut on-site to custom-fit each vessel, beat into shape and place with a hammer, and sometimes cut into small pieces to fit through access openings to the work areas, with this being particularly an issue for irregularly shaped vessels.

Other refractory anchoring devices and systems include D-BAR anchors (e.g., U.S. Pat. No. 6,393,789), C-BAR anchors, and G3 anchors. Some of these are provided in sheet form and thus must by bent and cut to fit the individual vessel in the same manner as the HEXMESH sheets. And some of these include multiple parts that are interlocked together with a clinching system in the same manner as the HEXMESH sheets. As such, these other refractory anchoring devices and systems include some or all of the same drawbacks.

Accordingly, it can be seen that needs exist for improvements in anchoring devices, systems, and methods for refractory liners for thermal vessels. It is to the provision of solutions to these and other problems that the present invention is primarily directed.

SUMMARY

Generally described, the present invention relates to refractory anchoring devices having unenclosed semi-hexagonal cell openings. The refractory anchoring devices each include a main body and a mounting feature for mounting to a thermal vessel. The main body has the shape of two end-to-end Y's forming a central segment, two branch segments extending at an obtuse angle from each of the two ends of the central segment, and an extension segment extending at an obtuse angle from each of the four branch segments, to collectively form four unenclosed cell openings that are each semi-hexagonal in shape. Some embodiments include four reinforcement segments with each one extending into a respective cell opening, four voids with each one extending through respective adjacent branch and extension segments, an underbody gap formed under the central segment for refractory interlinking between cell openings, and/or a single stud-welding cylinder for the mounting feature.

Another aspect of the invention relates to refractory anchoring systems that include an array of refractory anchoring devices having unenclosed semi-hexagonal cell openings. The refractory anchoring devices are arranged in the refractory anchoring systems so that the unenclosed semi-hexagonal cell openings of adjacent ones of the anchoring devices cooperate to form substantially hexagonal cells and provide flow passageways for the refractory to interconnect the cells.

And another aspect of the invention relates to refractory lining methods that use an array of refractory anchoring devices having unenclosed semi-hexagonal cell openings. The method includes mounting the refractory anchoring devices in an arrangement to form refractory anchoring systems with the unenclosed semi-hexagonal cell openings of adjacent ones of the anchoring devices cooperating to form substantially hexagonal cells and provide flow passageways for the refractory to interconnect the cells. In some embodiments, the refractory anchoring devices include a single stud-welding stud for a mounting feature and the mounting process includes stud-welding the anchor devices in place (for example using BRANDTECH precision welding equipment and processes).

These and other aspects, features, and advantages of the invention will be understood with reference to the drawing figures and detailed description herein, and will be realized by means of the various elements and combinations particularly pointed out in the appended claims. It is to be understood that both the foregoing general description and the following brief description of the drawings and detailed description of example embodiments are explanatory of example embodiments of the invention, and are not restrictive of the invention, as claimed.

BRIEF DESCRIPTION OF THE DRAWINGS

FIG. 6 is an end view of the refractory anchor of FIG. 1.
FIG. 7 is a perspective view of a refractory anchor according to a second example embodiment of the invention.
FIG. 8 is another perspective view of the refractory anchor of FIG. 7.
FIG. 9 is another perspective view of the refractory anchor of FIG. 7.
FIG. 10 is a top view of the refractory anchor of FIG. 7.
FIG. 11 is an end view of the refractory anchor of FIG. 10.
FIG. 12 is a side view of the refractory anchor of FIG. 10.
FIG. 13A is a perspective view of the first anchoring system of FIG. 13 showing the installed refractory, with portions removed to reveal the underlying anchors, forming generally hexagonal, interlinked cells.

DETAILED DESCRIPTION OF EXAMPLE EMBODIMENTS

Figure 1:
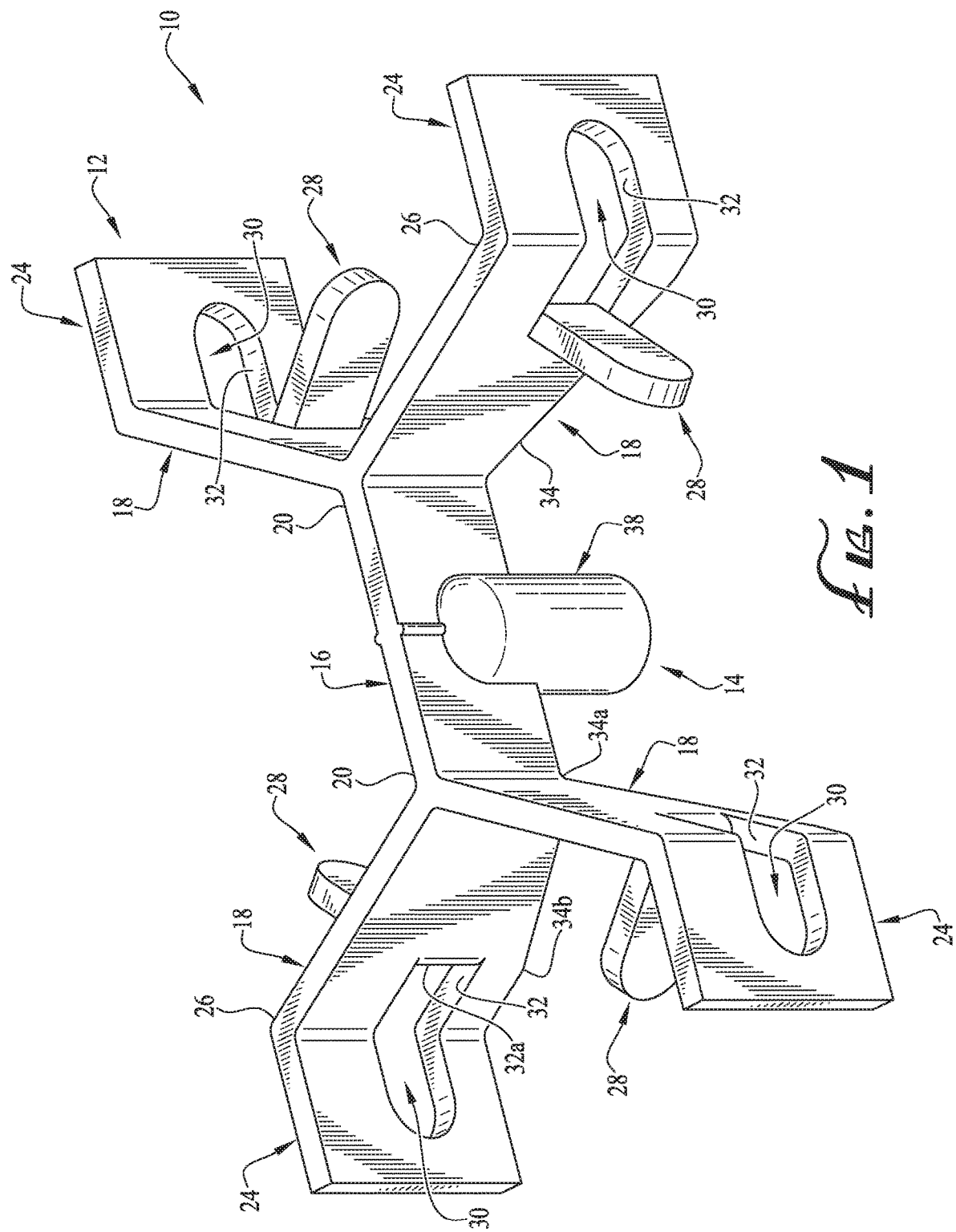
FIG. 1 is a perspective view of a refractory anchor according to a first example embodiment of the invention.
Figure 2:
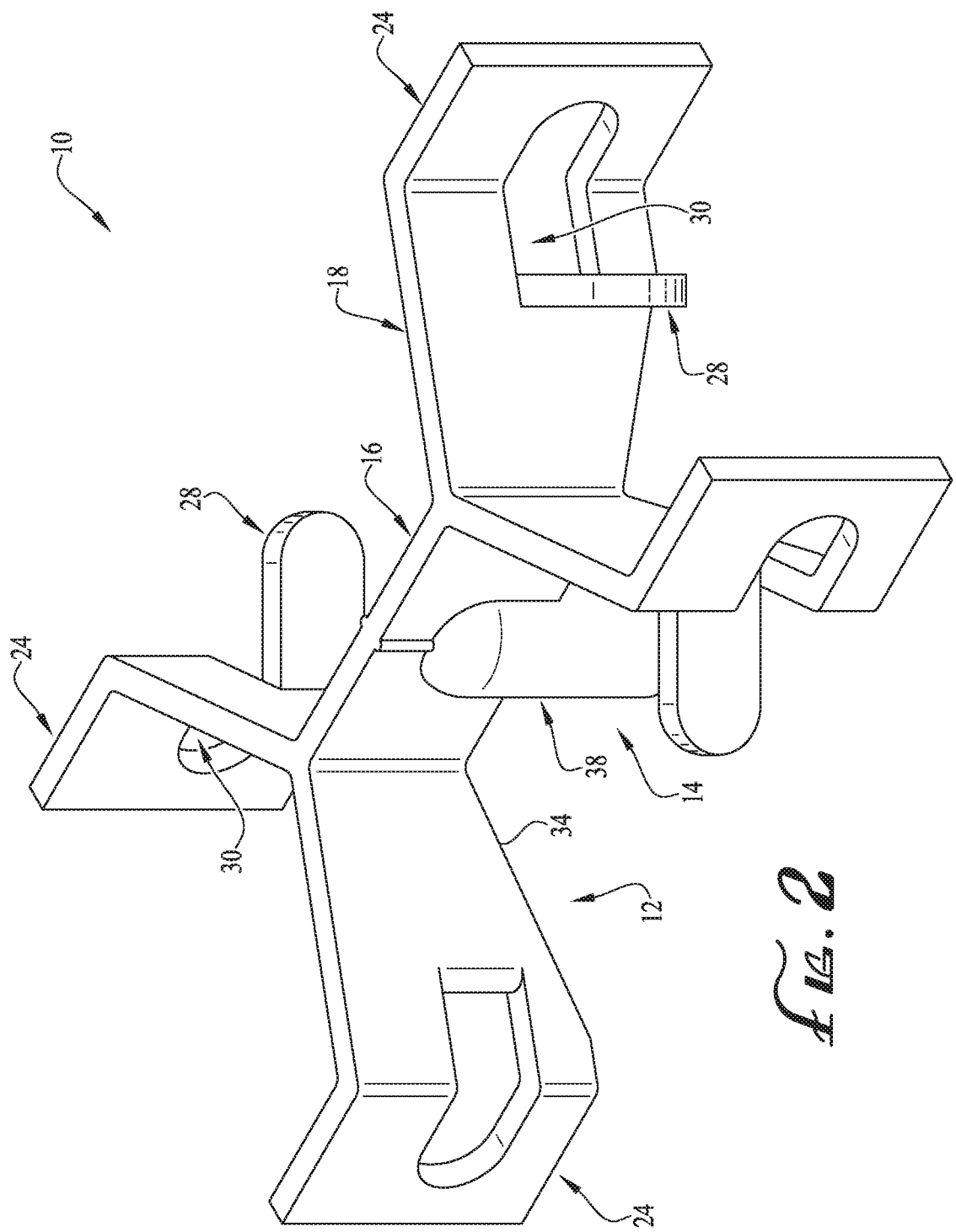
FIG. 2 is another perspective view of the refractory anchor of FIG. 1.

Generally described, the present invention relates to an anchoring device, system, and method for a refractory material for together forming a protective barrier system for a thermal vessel. The anchoring device, system, and method can be used for protecting thermal vessels such as high-temperature cyclone separators (e.g., fluid catalytic crackers aka FCCs), burners, furnaces, columns, and tanks, piping for these, and other high-temperature industrial-process containers. These thermal vessels operate at high temperatures of typically about 250 C to about 1800 C. The anchoring device, system, and method can be used for protecting such thermal vessels in oil refineries, other petrochemical-process facilities, chemical-process facilities, chemical-manufacturing plants, cement plants, fertilizer plants, steel mills, pulp-and-paper plants, power-generating plants, and other facilities and industries using such high-temperature vessels. And the anchoring device, system, and method can be used for anchoring refractory materials including concrete, fibers, plastics, ceramics, and/or other conventional refractories, typically applied in a viscous state and cured on site, but in some embodiments precast or otherwise pre-formed.

Referring to the drawings, FIGS. 1-6 show a thin-layer abrasion-resistant refractory anchoring device 10 according to a first example embodiment of the invention. The anchor 10 includes a main body 12 having the shape of two "Y"s arranged end-to-end (and thereby defining two side/central semi-hexagonal (trapezoidal) openings and two end triangular openings) and a mounting element or feature 14 for mounting the main body 12 to the thermal vessel (not shown) to be protected.

The main body 12 includes a central segment 16 (i.e., the aligned and continuous base legs of the two end-to-end "Y"s) and four branch segments 18 extending from the central segment 14 (i.e., the two pairs of splayed upper legs of the two end-to-end "Y"s) with a first pair of the branch segments 18 extending from a first part of the central segment 14 and with a second opposite pair of the branch segments 18 extending from a second part of the central segment 14 that is spaced apart from the first part. In the depicted embodiment, for example, the two branch segment pairs 18 extend from opposite outer end portions 20 of the central segment 16. In some embodiments, the branch segments extend from the central segment before its end edges (with the central segment extending into the end openings) or are otherwise configured.

The four branch segments 18 are each angled with respect to the central segment 14 at an obtuse angle to form four unenclosed cell openings (e.g., notches or recesses) 22 between them. In the depicted embodiment, for example, each of the four branch segments 18 is arranged at an obtuse angle $\alpha$ of about 120 degrees from the central segment 14 in a substantially symmetrical configuration, which leaves an obtuse angle $\beta$ of about 120 degrees between the two branch segments 18 at each end portion 20 of the central segment 14. In other embodiments, the branch segments extend from the central segment all at the same larger or smaller obtuse angle, at two to four different angles from each other, or in another configuration.

In addition, the main body 12 of typical embodiments further includes one or more extension segments 24 extending from one or more of the branch segments 18. In the depicted embodiment, for example, the main body 12 includes four extension segments 24 with each one extending from a respective one of the four branch segments 18. Typically, the extension segments 24 extend from outer end portions 26 of the respective branch segments 18. In some embodiments, the extension segments extend from the branch segments before their end edges (with the branch segments extending beyond where the extension segments extend from) or are otherwise configured. And in some embodiments, the main body does not include any extension segments.

The four extension segments 24 are each angled relative to their respective branch segments 18 at an obtuse angle to define portions of the two opposite end openings 22. In the depicted embodiment, for example, each of the four extension segments 24 is arranged at an obtuse angle $\theta$ of about 120 degrees from the respective branch segment 18 in a substantially symmetrical configuration, leaving the extension segments 24 substantially parallel with the central segment 16. As such, each pair of the branch segments 18 and the central segment 16 are symmetrically arranged, with each one of these three segments at 120 degrees from the other two of these three segments. In other embodiments, the extension segments extend from the branch segments all at the same larger or smaller obtuse angle, at two to four different angles from each other, or in another configuration.

Figure 3:
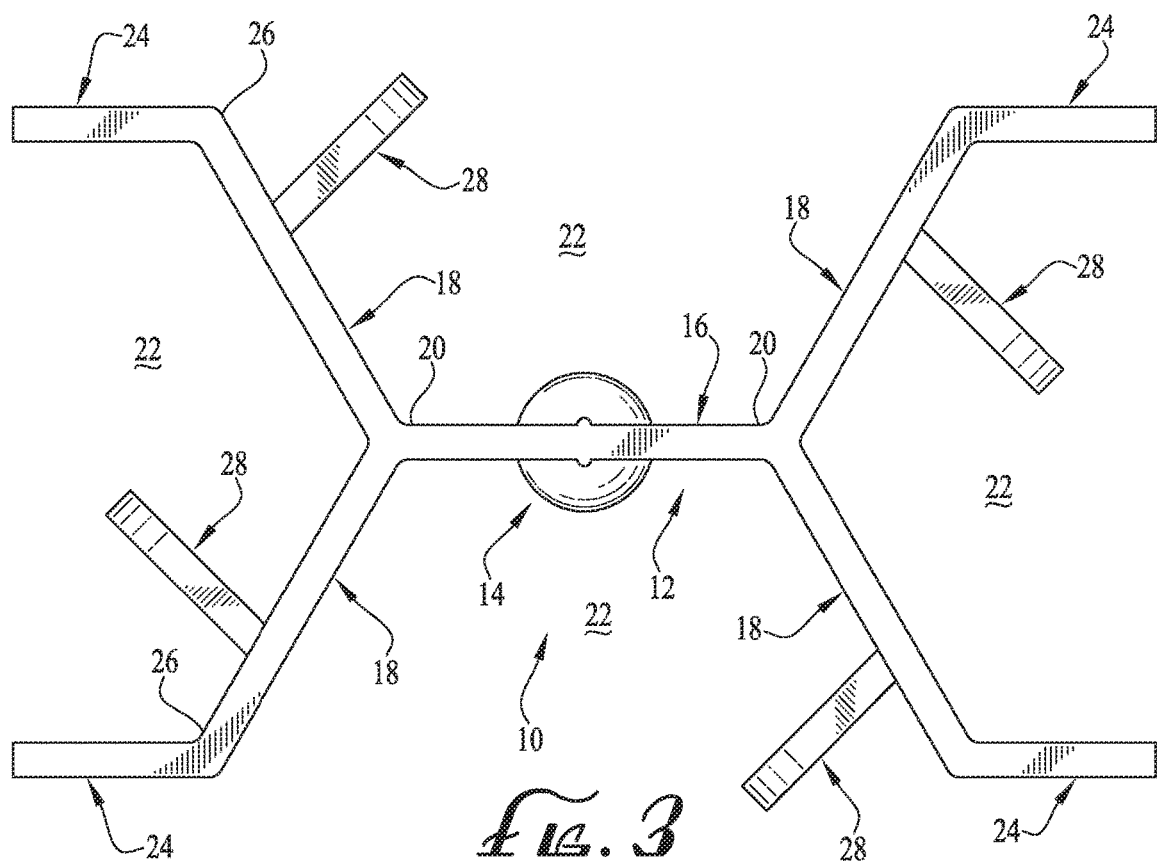
FIG. 3 is a top view of the refractory anchor of FIG. 1.
Figure 5:
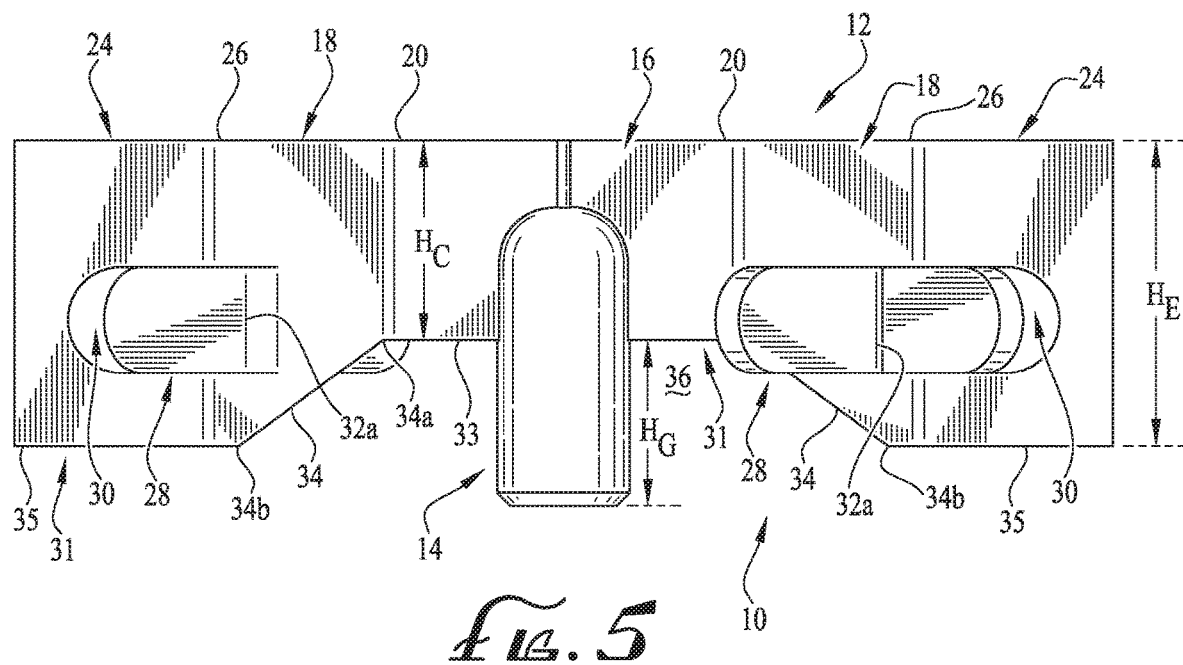
FIG. 5 is a side view of the refractory anchor of FIG. 1.

In this substantially symmetrical configuration, with the branch segments 18 extending from the central segment 16 and the extension segments 24 extending from the branch segments 18 all at substantially the same obtuse angle, all four of the openings 22 are semi-hexagonal (the extension segments making the triangular end openings into semi-hexagonal openings). In the depicted embodiment, for example, the two opposite end semi-hexagonal openings 22 are formed by one end pair of the branch segments 18 (defining two adjacent full-length sides of a hexagon) and by one end pair of the extension segments 24 (defining two opposite/facing half-length sides of a hexagon), as shown in FIGS. 3 and 6. And the two opposite central semi-hexagonal openings 22 are formed by the central segment 16 (defining one full-length side of a hexagon) and two of the branch segments 18 (one of each end pair; each one defining one full-length side of a hexagon), as shown in FIGS. 3 and 5. Thus, the end semi-hexagonal openings 22 and the central semi-hexagonal openings 22 are rotationally shifted by about 60 degrees with respect to each other so that they are arranged together in a tessellated fashion.

To provide further symmetry in the configuration of the anchor 10, each of the branch segments 18 typically has a length that is substantially the same as that of the central segment 16 (with all of the branch segments 18 having the same length), and each of the extension segments 24 typically has a length that is about half (or less than about half) that of the central and branch segments 16 and 18 (with all of the extension segments 24 having the same length). In this way, each of the unenclosed cell openings 22 defines a regular (equilateral) semi-hexagonal shape of the same size/area, so that a number of the anchors 10 can be arranged together with any one of the four cells/openings 22 of one anchor cooperating with any one of the four cells/openings of an adjacent anchor to form a substantially hexagonal cell, thereby reducing the likelihood of biscuiting. In typical embodiments, for example, the length of the central and branch segments 16 and 18 (and twice the length of the extension segments 24) is about 20 mm to about 30 mm (e.g., about 25 mm), with the openings 22 thus being about 50 mm to about 60 mm (e.g., about 55 mm) across (e.g., between the extension segments 24 of each end pair).

Figure 16:
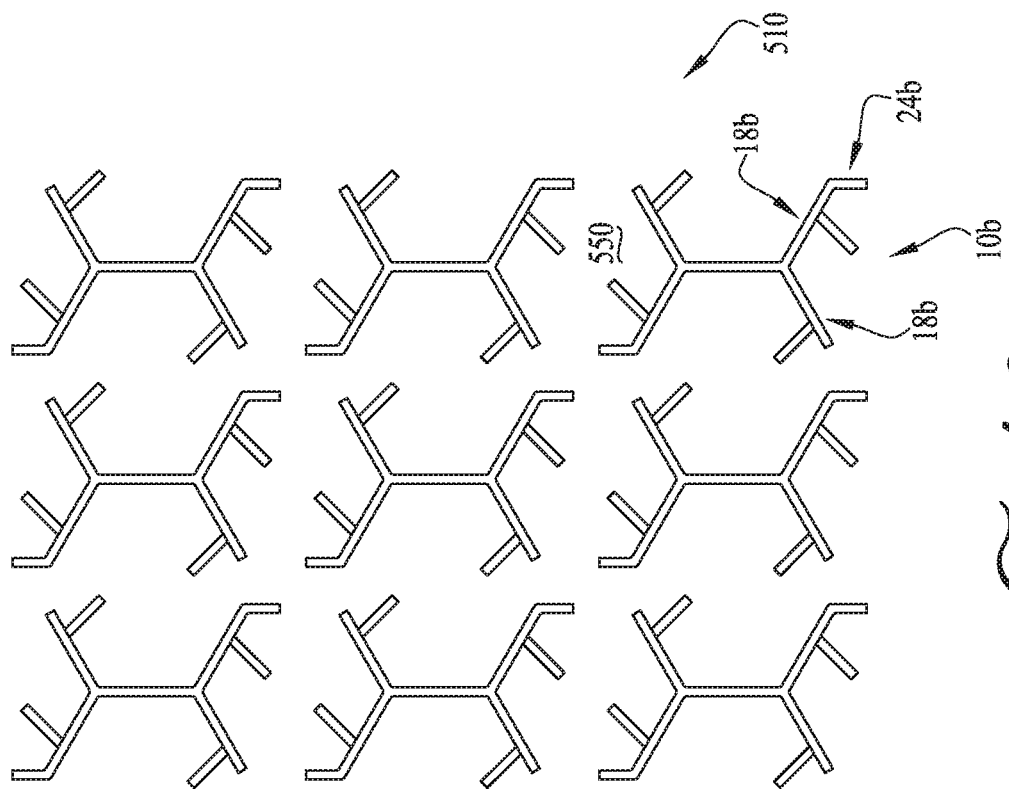
FIG. 16 is a top view of a fourth anchoring system of modified/alternative refractory anchors according to a fourth example embodiment.
Figure 15:
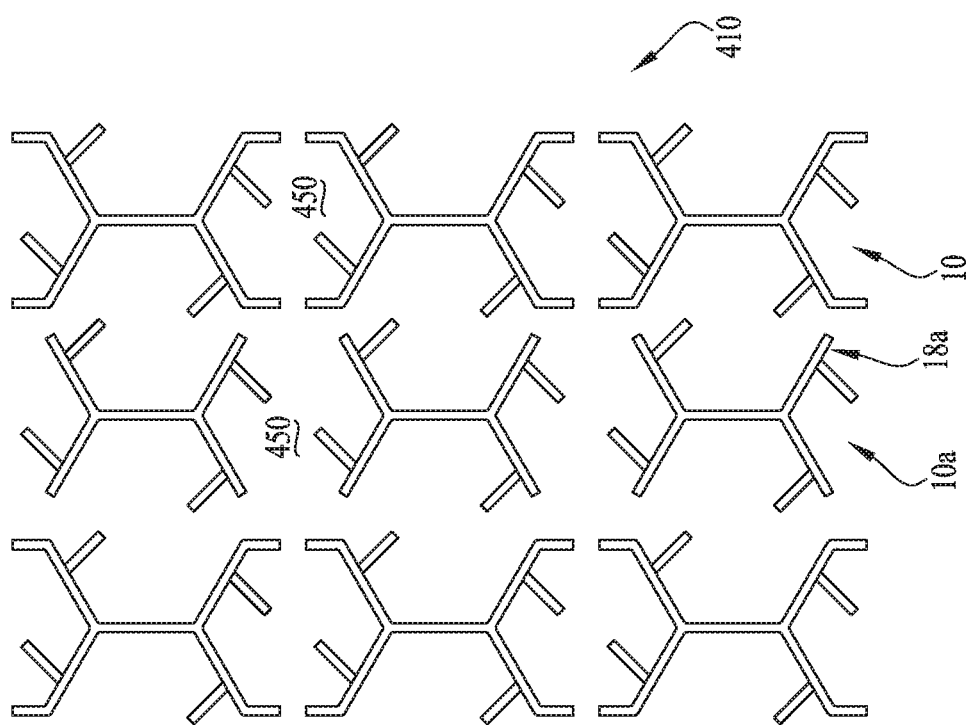
FIG. 15 is a top view of a third anchoring system of the anchors of FIG. 1 and modified/alternative refractory anchors according to a third example embodiment.
Figure 17:
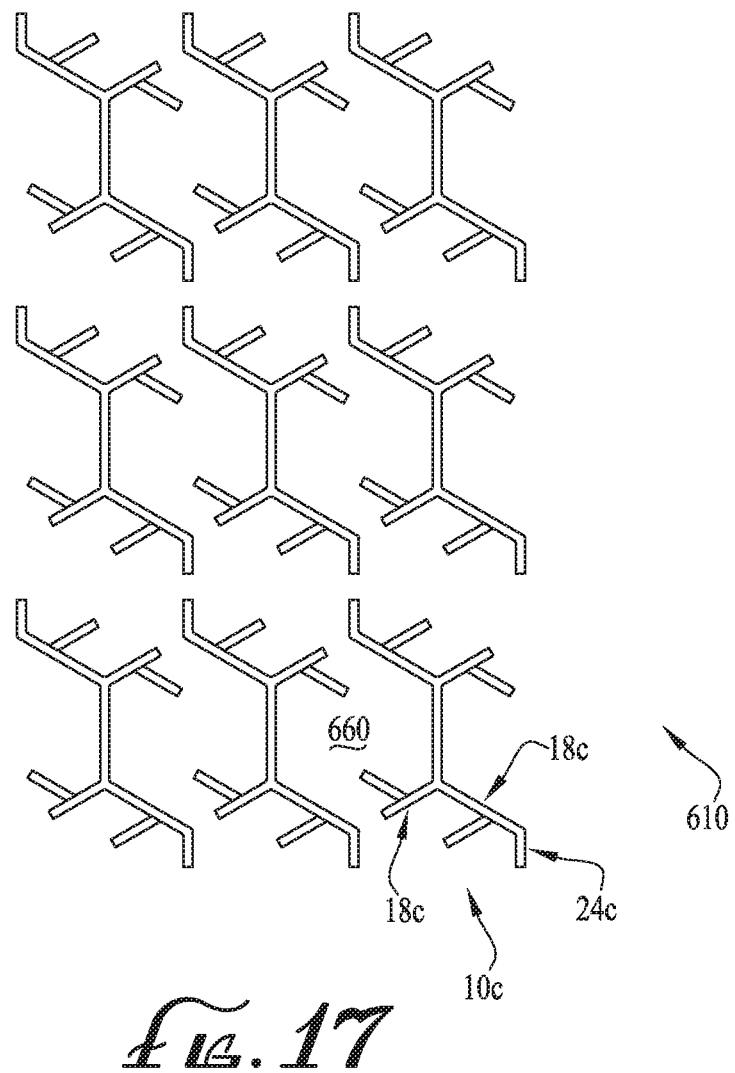
FIG. 17 is a top view of a fifth anchoring system of modified/alternative refractory anchors according to a fifth example embodiment.

In other embodiments, the central, branch, and/or extension segments all have a longer or shorter length, have different lengths from each other, or are provided with other lengths as may be desired. For example, in some embodiments the extension segments are shorter than one-half the length of the central and/or branch segments, so that two anchoring devices can be arranged end-to-end adjacently but spaced apart in an anchoring system (in the manner shown in FIG. 13, except with shorter extension segments), and the adjacent end openings of the two anchors cooperate to form a regular hexagonal cell (though not fully enclosed because of the end-to-end spacing between the anchors), for example as shown in FIG. 15. And in other embodiments, only one of the branch segments at each end has an extension segment extending from it (so there are two extension segments, one at each end of the anchor), so that two anchoring devices can be arranged side-to-side immediately adjacently (e.g., with nominal spacing sufficient to avoid contacting during thermal expansion and contraction during use) in an anchoring system (in the manner shown in FIG. 13, except with no side-to-side spacing), with each extension segment positioned at a branch segment of the adjacent anchor without an extension segment (to fill the position where an extension segment was not included in that anchor), and the adjacent central/side openings of the two anchors cooperate to form a regular hexagonal cell (with nominal spacing sufficient to avoid contacting during thermal expansion and contraction during use), for example as shown in FIGS. 16 and 17.

In addition, the main body 12 of typical embodiments further includes one or more reinforcement segments 28 extending into one or more of the four openings 22. In the depicted embodiment, for example, the main body 12 includes four reinforcement segments 28 with each one extending into a respective one of the four openings 22 so that each of the four openings 22 has a respective reinforcement segment 28 extending into it. In example embodiments, the reinforcement segments 28 each are generally linear and have a length of about 10 mm to about 20 mm (e.g., 15 mm), though they can be provided in other regular or irregular shapes, sizes, and/or configurations, as may be desired for an application. The reinforcement segments 28 are thus in addition to the symmetrical semi-hex arrangement of the two branch segments 18 and the two extension segments 24 at each end of the anchor, and do not define any portion of the semi-hex openings 22. The reinforcement segments 28 provide additional contact surface area for engaging and securing the refractory in place, and they protrude into the unenclosed cell openings 22 to reduce the unobstructed distance across the openings 22, thereby better securing the refractory in the cells and helping reduce the likely incidence of biscuiting of the refractory.

The reinforcement segments 28 are each typically non-perpendicularly angled from the branch segment 18 they extend from and non-parallel to the adjacent branch segment 18 (on the same end of the same anchor 10, with these two branch segments together forming one Y-shaped end of the main body 12) so that they extend into the respective openings 22 in a non-symmetrical manner. The non-perpendicular arrangement of the reinforcement segments 28 can be implemented, for example, by the reinforcement segments 28 being oriented/arranged at about 75 degrees relative to the branch segment 18 they extend from, and thus at an angle φ of about 45 degrees relative to the central segment 16 (see FIG. 4). This non-perpendicular arrangement of the reinforcement segments 28 avoids right angles in an effort to decrease the likelihood of biscuiting and at the same time it forms "pinch" or "catch" surfaces that help retain the refractory material in the openings 22.

Figure 13:
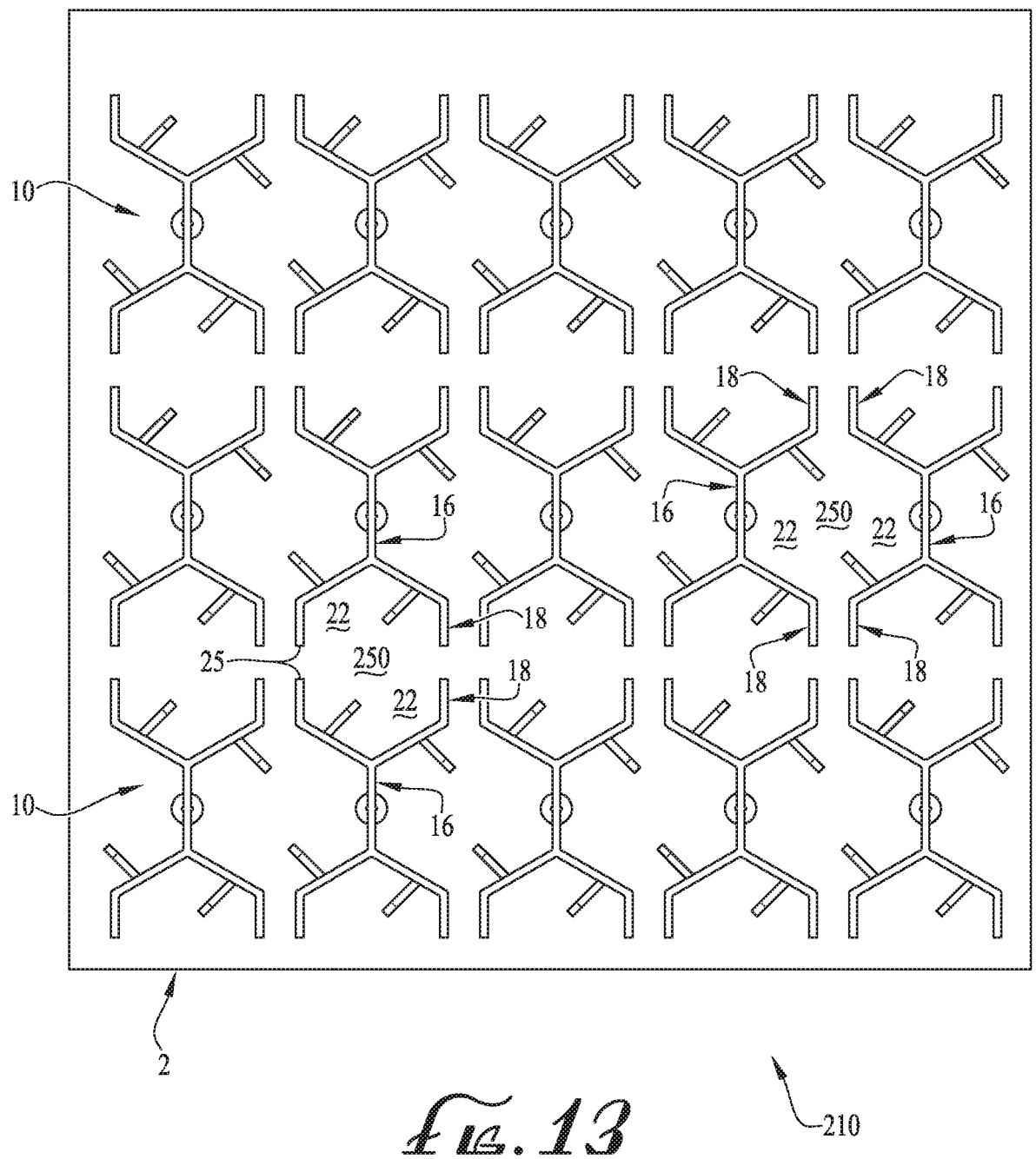
FIG. 13 is a top view of a first anchoring system of the refractory anchors of FIG. 1.

Furthermore, when the anchors 10 are installed into a symmetrically arrayed system forming generally hexagonal cells 250, for example the anchor system 210 of FIG. 13, this non-perpendicular arrangement of the reinforcement segments 28 results in the reinforcement segments 28 of adjacent anchors 10 being parallel but not in linear alignment. This avoidance of adjacent-anchor reinforcement segments 28 being linearly arranged thereby avoids creating linear seams in the refractory material, which linear seams can over time form cracking zones where the refractory material tends to fail.

In addition, the main body 12 includes voids 30 that provide additional contact surface area (the void-defining exposed through-surfaces 32 of the respective main-body segments) for engaging and securing the refractory in place. In this way, the reinforcement segments 28 and the void through-surfaces 32 provide better retention/anchoring of the refractory material (more contact surface area), and the voids 30 provide for interlinking of the refractory material (which typically is flowable during installation through the voids into and extending between adjacent cells) so it is not isolated into individual cells, to provide even better retention/anchoring of the refractory material and further avoid biscuiting.

In one-piece cast embodiments, the reinforcement segments 28 and the voids 30 can have the same configuration (size and shape, though positive/solid and negative/void), as depicted, or they can have similar or different configurations if desired. In other one-piece embodiments, the reinforcement segments can be formed by portions of the main body that are angled from the adjacent/remainder portions of the main body to leave behind the voids in the main body that typically have substantially the same configuration as the respective reinforcement segment that vacated that void. And in other embodiments, the reinforcement segments are separate pieces attached to the main body, with or without inclusion of the voids.

In addition, the voids 30 typically each extend continuously through adjacent ones of the branch segments 18 and the extension segments 24 that are angled relative to each other, with the lateral through-surfaces 32 of the respective main-body segments 32 (which peripherally define the voids 30) thus extending continuously through the adjacent branch and extension segments 18 and 24 and thus having two angled portions, for the refractory to flow through during installation to interconnect adjacent cells and to provide more surface-area engagement for further-enhanced securement of the refractory in place. In other embodiments, the voids extend continuously through the central and branch segments, or continuously through the central, branch, and extension segments.

Figure 4:
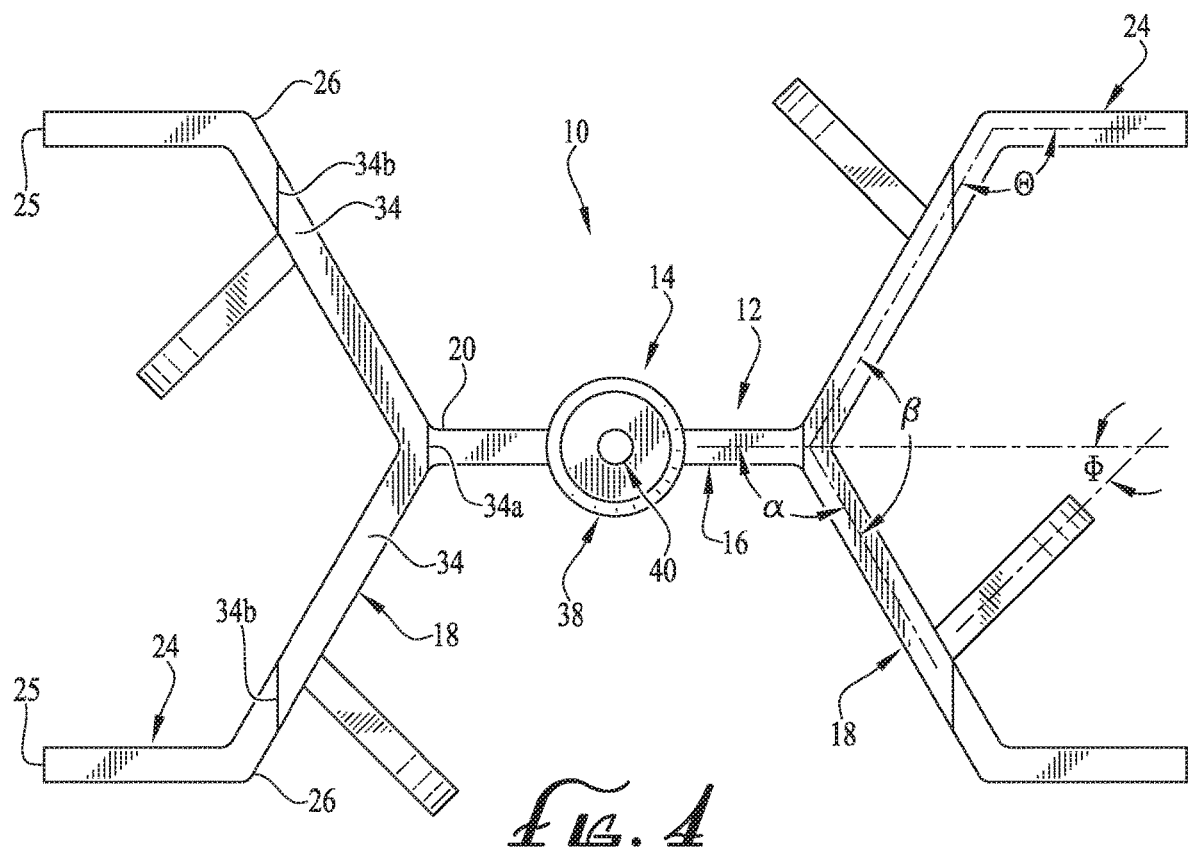
FIG. 4 is a bottom view of the refractory anchor of FIG. 1.

Furthermore, the main body 12 typically defines underbody gaps 36 between the bottom 31 of the main body 12 (e.g., at least a portion of the central segment 16 and typically also a portion of the branch segments 18) and the vessel shell (when at least portions of the bottoms of the extension segments 24 are positioned substantially flush against the vessel shell, including direct contact and immediately adjacent such as within about 0.2 mm). For example, the bottom side (surface or edge) 31 of the main body 12 can include an elevated portion 33 (spaced from the vessel shell) at a laterally inner portion of the main body (e.g., at least a portion of the central segment 16), a base portion 35 (flush against the vessel shell) at a laterally outer portion of the main body (e.g., at least a portion of the extension segments 24), and a transition portion 34 between and connecting them (e.g., ramped (e.g., linear or curved) along at least a portion of the branch segments 18 and ramped upward toward the central segment) to form the resulting underbody gaps 36, for instance as shown in FIGS. 4-5. These underbody gaps 36 allow the refractory to flow (during installation) under the central segments 16 of the anchor 10 (and typically under portions of the branch segments 18) to interlink the refractory material (after curing) in the opposite side cells 22 (and also typically in the opposite end cells 22) so it is not isolated in any individual cell to provide even better retention/anchoring of the refractory material and further avoid biscuiting.

In the depicted embodiment, the main body 12 has a substantially level (e.g., planar or irregular) top side (surface or edge), with the central segment 16 (or at least a portion of it) having a height dimension $H_C$ that is smaller than a height dimension $H_E$ of the extension segments 24 (or at least a portion of them), so that the underbody gaps 36 are formed under the central segment 16 but not under the extension segments 24. As examples, the central segment 16 height $H_C$ can be about 15 mm to about 20 mm (e.g., about 17 mm) and the extension segments 24 height $H_E$ can be about 20 mm to about 25 mm (e.g., about 23 mm), with the underbody gaps 36 typically having a height $H_G$ of about 4 mm to about 6 mm (and thus with the thin-layer refractory material typically having a thickness/height of about 20 mm to about 25 mm. Also, with the underside gaps 36 being laterally centrally/inwardly located, the more outwardly located extension segments 24 (or at least portions of them) contact the vessel shell, which provides a laterally wide footprint or support base for stability of the anchor 10 in its mounting position. In other embodiments, the bottom surface of the main body is scalloped, notched, or otherwise shaped to define the underbody gaps.

Each bottom ramped transition 34 runs from a laterally inner location 34a and outwardly (away from the central segment 16) to a laterally outer location 34b. The inner locations 34a can be for example at (as depicted) or near where the branch segments 16 angle from the central segment 16 (i.e., the opposite laterally outer ends 20 of the central segment 16). And the outer locations 34b of the bottom ramped transitions 34 can be for example at or near (as depicted) where the extension segments 24 angle from the respective branch segments 18 (i.e., the opposite laterally outer ends 26 of the branch segments 18). As shown in FIGS. 4-5, the outer/end locations 34b of the bottom ramped transitions 34 can be on the branch segments 16, laterally inward of the extension segments 24, so that there is relatively little/nominal lateral overlap between the underbody gaps 36 and the body voids 30 (which typically extend through the extension segments 24 and the branch segments 18). For example, at least a portion of the end location 34b of the bottom ramped transition 34 can be substantially vertically (axially) aligned with (or slightly laterally inward from, toward the central segment 16) the inner edges 32a of the void-defining through-surfaces 32, as best shown in FIGS. 4 and 6. This arrangement provides a good underflow area (formed by the laterally inward underbody gaps 36) and a good through-flow area (formed by the laterally outward body voids 306) for the refractory (during installation) without sacrificing the structural integrity of the main body 12 (specifically, the extension segments 24 and the branch segments 18 where the voids 30 are located), for better refractory flow-through and retention in the anchor-formed cells.

In this embodiment, this arrangement provides at least one flow passageway from the central segment 16, along the entire length of the respective branch segments 18, and to the respective extension segments 24, extending around the bend between the central and branch segments 16 and 18 and around the bend between the branch and extension segments 18 and 24, because the flow-through passageways (through the body 12 via the voids 30) and the flow-under passageways (under the body 12 via the gaps 36) at least nominally laterally overlap (including their ends being vertically aligned, for example adjoining and in alignment with the attached end of the respective reinforcement segment 28). In other embodiments, the body voids and the under-body gaps do not laterally overlap but they nevertheless extend between the central and branch segments, between the branch and extension segments, and along the majority of the length of these three anchor segments for better refractory flow-through and retention in the anchor-formed cells, for example continuously except where interrupted by the presence of reinforcement segments 28.

Figure 5A:
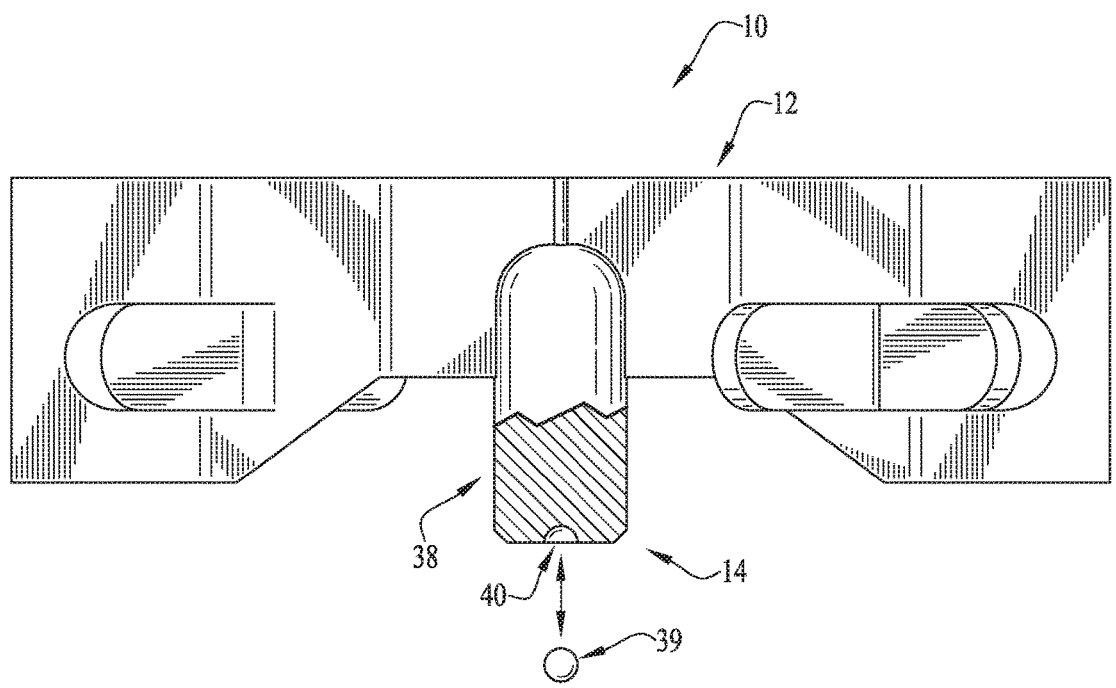
FIG. 5A shows the refractory anchor of FIG. 5 with a welding stud shown in cross section.

Turning now to the mounting element or feature 14, it is designed for mounting the anchor 10 to the thermal vessel (not shown) to be protected. In the depicted embodiment, and referring particularly to FIG. 5A, the mounting feature 14 is designed for conventional stud-welding installation methods and equipment, and it thus includes a stud (e.g., a cylinder) 38 defining a recess (e.g., a semi-spherical tap hole) 40 for receiving a metal interface/pilot element (e.g., a solid ball) 39. The interface/pilot element 39 is made of a different material (relative to the stud 38) that has a lower melting point so that it melts before the stud 38 for optimal stud-welding. For example, the anchor 10 can be made of steel and the interface/pilot ball can be made of aluminum. Because of this, the interface/pilot element 39 is a separate component (relative to the stud 38 and to the rest of the anchor 10) in one-piece anchor embodiments.

The stud 38 and the interface/pilot element 39 can have a configuration of a conventional type as is suitable for conventional one-step stud-welding techniques, so additional details are not provided for brevity. And the mounting feature 14 can typically include a single stud 38 positioned at the center of the central segment 16 of the main body 12, with no other attachment of the anchor to the vessel shell (the extension segments 24 typically contact the vessel shell for stability without being attached), so that vessel expansion and contraction does not stress the weld and weaken it. It will be understood that although the stud 38 extends below the main-body extension segments 42 in FIGS. 5-6, during stud-welding installation of the anchor 10, the bottom of the stud 38 is quickly heated and melted into a molten pool so that, upon completion of the installation, the bottoms of the extension segments 42 are immediately adjacent (i.e., contacting or within a fraction of a millimeter of contacting) the vessel shell. Also, the extra length of the stud 38, the bevel at the free end of the stud 38, and the interface/pilot element 39 being diametrically centered on the free end of the stud 38, ensure that, during stud-welding installation, the arc opens to the stud 38 (and not to the anchor main body 12) to quickly heat and melt the interface/pilot element 39, and then the stud 38 quickly heats further and melts evenly. In other embodiments, mounting feature is configured for manual welding or other conventional anchor attachment methods known in the art.

Turning now to the construction of the anchor 10, in typical embodiments the main body 12 and the welding stud 38 are made of a single component piece of a material, such as a metal alloy (e.g., carbon steel or stainless steel such a 300 or 600 series) with a substantially uniform thickness (e.g., about 2.5 mm), that is sand-cast (or otherwise fabricated by single-use molds) into a one-piece part. Because the anchor 10 is a single piece, no clinching mechanisms are needed to fasten multiple parts together, thereby eliminating a point of failure and simplifying manufacture. Also, because of the one-piece construction, the anchors 10 are modular and individually installed so that the effects of vessel expansion and contraction are minimized to help reduce the risk of biscuiting. In other embodiments, the anchor can be made of other materials and in multiple parts assembled together, or by other fabrication techniques such as other types of casting or forging, as may be desired.

Referring now to FIGS. 7-12, there is shown a thin-layer abrasion-resistant refractory anchoring device 110 according to a second example embodiment of the invention. The anchor 110 is a half-unit version (of the full-unit anchor 10 described above) for installation at the ends/edges of the surface area of the vessel shell that is to be protected (as described below) so that areas too small for a full-unit anchor 10 can still be protected without cutting and trimming an anchor down to size. As such, the anchor 110 includes a main body 112 and a mounting feature 114 for mounting to the thermal vessel to be protected. The mounting feature 114 can be of the same design as that of the first embodiment, and the main body 112 can be of the same design as the first embodiment except as detailed below.

In this half-unit design, the main body 112 includes a central segment 116, two branch segments 118 extending from the central segment 116 (e.g., at spaced apart locations), two oppositely arranged extension segments 124 extending from the respective branch segments 118, and two reinforcement segments 128 (e.g., formed from adjacent branch and extension segments 118 and 124). The central segment 116, branch segments 118, extension segments 124, and reinforcement segments 128 can be of the same design as those of the first embodiment, except that each end of the main body 112 has only one (instead of two) of the branch, extension, and reinforcement segments 118, 124, and 128. The ramped transition 134 and other common features are typically also embodied in the anchor 110. Additional details of the anchor 110 can be included, as will be understood by persons of ordinary skill in the art, but they are not repeated for brevity and clarity.

In another aspect, the invention relates to systems of plural thin-layer abrasion-resistant refractory anchoring devices. The systems include a number of refractory anchors having unenclosed semi-polygonal cell openings, for example the full-unit anchors 10, the half-unit anchors 110, and/or any of the other anchors 10a-e disclosed herein, and in some embodiments can additionally or alternatively include other refractory anchors having unenclosed cell openings in semi-hexagonal or other semi-polygonal shapes. In the depicted embodiments, the refractory anchoring devices are arranged in the refractory anchoring systems so that the unenclosed semi-hexagonal cell openings of adjacent ones of the anchoring devices cooperate to form substantially hexagonal cells (including regular hexagonal shapes and oblong ones) for retaining the refractory. In other embodiments, such refractory anchors can be arranged into systems to form cells having other polygonal shapes for retaining the refractory. Examples of such anchoring systems are shown in the figures described below, which are representative for explanatory purposes only and really only show portions of such anchoring systems and vessels, which are typically much larger and form an enclosure defining the thermal-process environment to be protected.

FIGS. 13 and 13A show a first system 210 of the full-unit anchors 10 mounted to a vessel shell 2 in a first arrangement and ready for application of the refractory 4. In this system 210, the anchors 10 are arranged in an ordered array of rows and columns to cooperatively define an ordered array of generally hexagonal cells 250 in a tessellated pattern. Each of the generally hexagonal cells 250 is formed by two adjacent ones of the semi-hexagonal openings 22 of adjacent anchors 10, with each of the cells 250 having all six hexagonal sides formed at least in part by a segment (central 16, branch 18, or extension 24) of one of the anchors 10. As depicted, there are spaces between the adjacent anchors 10 (so the cells 250 are not completely bounded or "closed," and are thus at least partially open), however, at least four of the six hexagonal cell sides are formed in their entirely by one of the anchor segments, and no more than two are not, with those two hexagonal cell non-contiguous (i.e., open) sides having the majority of their lengths formed by two adjacent anchor extension segments and the anchor spacings providing flow passageways between adjacent cells 250 for the refractory 4 to flow (during installation) and interlink the adjacent cells (after curing, for use).

The central segments 16 of each of the anchors 10 in each column are in substantial alignment, with the free ends/edges 25 of the extension segments 24 of adjacent anchors 10 in substantial alignment but spaced apart, so that the end openings 22 of adjacent anchors 10 in the same column together define one of the cells 250. The spacing between the adjacent extension-segment free ends/edges 25 in each column is far/large enough to ensure no physical contact during thermal expansion and contraction during high-temperature use and further to provide a passageway for refractory to flow during installation to interlink the refractory in adjacent end-formed cells, but typically close/small enough to maintain good surface contact between the anchors and the refractory by minimizing spaces in the cells free of any part of the anchors and further to keep the end-formed cells generally hexagonal. For example, the spacing between the extension segment ends/edges 25 is typically less than (or about the same as) the length of each of the extension segments 24 (e.g., about 5 mm to about 10 mm) but long enough that the end-formed cells 250 are slightly oblong in their generally hexagonal shape, as depicted. Without regard to forming substantially hexagonal-shaped cells 250, and based simply on industry standards, the spacing is usually about 2 mm to about 20 mm, typically about 10 mm to about 15 mm, and most typically about 15 mm.

And the central segments 16 of each of the anchors 10 in each row are in a side-by-side parallel alignment, with the extension segments 24 of adjacent anchors 10 in a side-by-side parallel alignment but spaced apart, so that the central/side openings 22 of adjacent anchors 10 in the same row together define one of the central-formed cells 250. The spacing between the adjacent parallel extension segments 24 in each row is far/large enough to ensure no physical contact during thermal expansion and contraction during high-temperature use and further to provide a passageway for refractory to flow during installation to interlink the refractory in adjacent central-formed cells, but typically close/small enough to maintain good surface contact between the anchors and the refractory by minimizing spaces in the cells free of any part of the anchors and further to keep the central-formed cells generally hexagonal. For example, the spacing between the adjacent parallel extension segments 24 in each row is typically about the same as the spacing between the adjacent extension-segment ends/edges 25 in each column such that the central-formed cells 250 are slightly oblong in their generally hexagonal shape, as depicted. Without regard to forming substantially hexagonal-shaped cells 250, and based simply on industry standards, the spacing is usually about 2 mm to about 20 mm, typically about 10 mm to about 15 mm, and most typically about 15 mm.

The result is an array of generally hexagonal refractory-holding cells that is installed without any time-consuming and/or difficult rolling or fitting steps required. Also, the risk of biscuiting is reduced because the individual anchors 10 are each individually mounted to the vessel shell 2 and spaced apart sufficiently that the thermal-stress effects of vessel expansion and contraction are minimized. Further, less metal anchor material is used (e.g., relative to HEX-MESH systems), for example because the anchors 10 are spaced apart in each column and in each row, and also by including optional features such as the body voids (e.g., flow-through passageways) and/or the underbody gaps (e.g., flow-under passageways). At the same time, though, a more robust anchor-and-refractory protective barrier system is achieved, for example because of the resulting six-sided hex cells, and also by including optional features such as the reinforcements (e.g., two in each resulting hex cell), the body voids (e.g., where the reinforcements vacated), and/or the underbody gaps (e.g., under the central segments). This helps extend the life of the anchor-and-refractory system, because the refractory protects the metal anchors from chemical attack, so less metal material means less opportunities/locations for potential failures. In this way, the flow passageways between adjacent semi-hex cells of adjacent anchors, including the body voids, the underbody gaps, and the adjacent-anchor spacings, provide the benefits of interlinked refractory for better holding/retention and of less metal used for less coking/failure.

In addition, because of the column-to-column spacing, and the row-to-row spacing, between the extension segments 24 of adjacent anchors 10, the resulting generally hexagonal cells 250 are not perfectly hexagonal but instead are slightly oblong (e.g., irregular or non-equilateral). (The cells 250 of this embodiment are generally hexagonal for familiarity to customers, but it is not necessary for the cells to be perfectly or even generally (including oblong) hexagonal in shape.) As depicted, for example, the generally hexagonal cells 250 formed by adjacent central openings are oblong/elongate and oriented at 90 degrees from the generally hexagonal oblong/elongate cells 250 formed by adjacent end openings (i.e., each oblong/elongate central-formed cell 250 is rotated by 90 degrees relative to the four adjacent oblong/elongate end-formed cells). In other embodiments, the extension segments are shorter than the central and branch segments so that even with the end-to-end spacing of adjacent anchors the resulting cells form regular/equilateral hexagons, for example as shown in FIG. 15.

Figure 14:
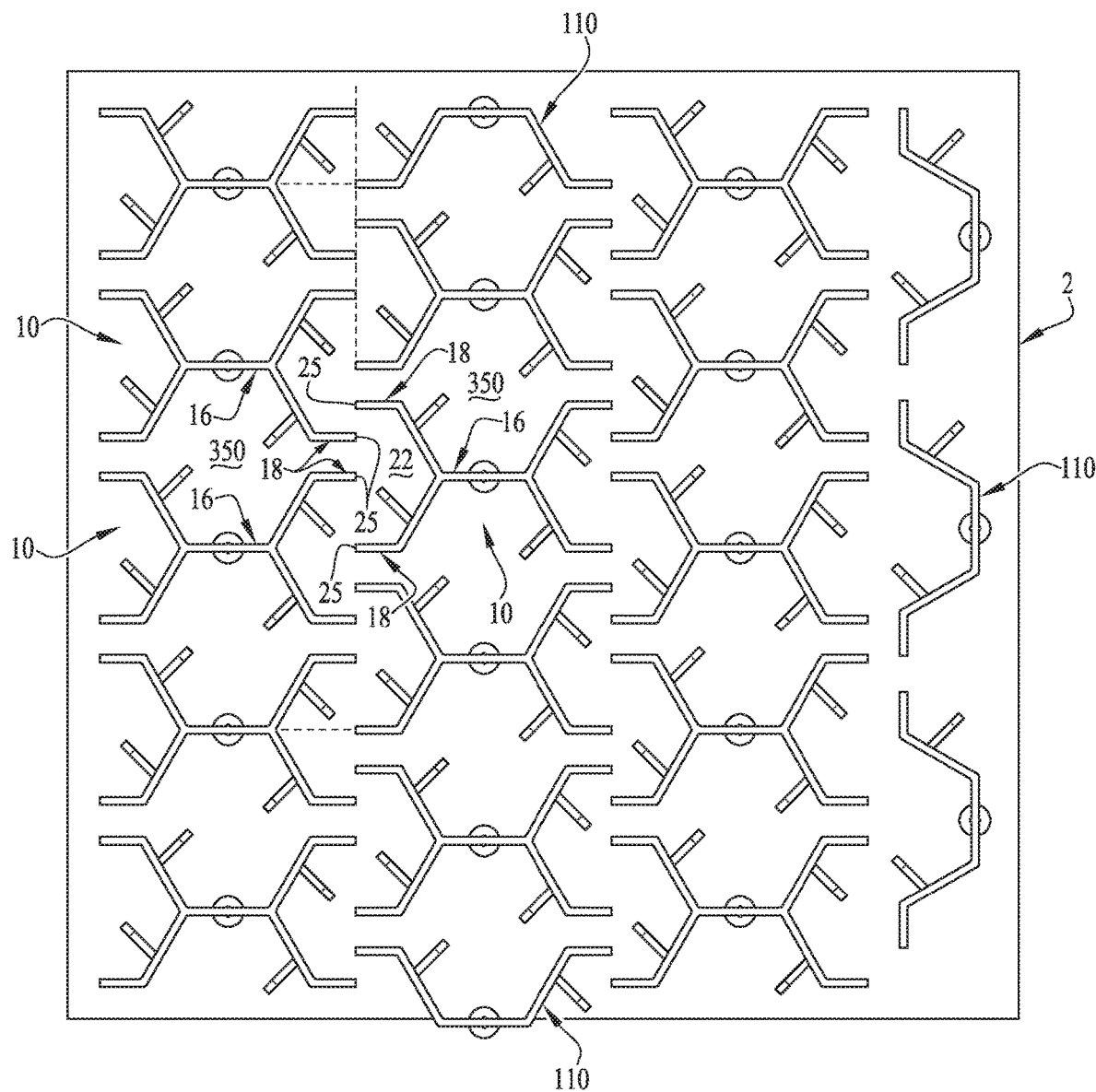
FIG. 14 is a top view of a second anchoring system of the refractory anchors of FIG. 1 and the refractory anchors of FIG. 7.

FIG. 14 shows a second system 310 of the full-unit anchors 10 and the half-unit anchors 110 mounted to a vessel shell 2 in a second arrangement and ready for application of the refractory. This second system 310 is similar to the first system 210, with the anchors 10 arranged in an ordered array to cooperatively define at least some substantially hexagonal cells 350 in a tessellated pattern, except as noted herein.

In particular, in this system 310, alternating columns of the anchors 10 are shifted or offset so that the central segments 16 of adjacent anchors 10 in adjacent columns do not align (in embodiments with a 90-degree-rotated anchor orientation, the rows are shifted/offset). Instead, the free/outer ends 25 of two extension segments 18 of adjacent anchors 10 in the same column are received in (or at the edge of) the end opening 22 of an adjacent anchor 10 in an adjacent column. For example, the free/outer edges 25 of the extension segments 18 of the anchors 10 in two adjacent columns can all be in an offset alignment with each other, as indicated by the vertical broken line in FIG. 14. Also, because of the presence of the reinforcement segments 24 in each of the end openings 22, the shift or offset can be less than one-half of an anchor, so that the central segment 16 of one anchor 10 is aligned with an extension segment 18 of an anchor in the adjacent column (instead of being centered between extension segments 18 of adjacent anchors 10 in the adjacent column), as indicated by the horizontal broken lines in FIG. 14. This eliminates the anchor extension segments 24 in each column being in alignment, as it can be desirable to avoid linearly arranged anchor segments that could contribute to formation of seams in the refractory that could be more prone to cracking and failing.

Furthermore, the system 310 additionally includes a number of the half-unit anchors 110 positioned at edges of the vessel surface 2 to be protected. These anchors 100 are well-suited for use to fill a margin that is too small for the full-size anchors 10, for example the half-unit anchors 110 can be oriented at 90 degrees relative to the full-size anchors 10 and arranged in a column, for example as shown in the right margin of FIG. 14. Also, the half-unit anchors 110 can be positioned at the ends of the columns of full-size anchors 10 that are offset or shifted, for example as shown at the top and bottom of the center column of full-unit anchors 10 of FIG. 14.

FIG. 15 shows a third system 410 of the anchors 10 and modified anchors 10*a* of a third example embodiment mounted to a vessel shell in a third arrangement and ready for application of the refractory. This third system 410 is substantially similar to the first system 210, with the anchors 10 and 10*a* arranged in an ordered array to cooperatively define some or all substantially hexagonal cells 450 in a tessellated pattern, except as noted herein.

In this system 410, the modified anchors 10*a* do not include the extension segments (which are included in the full units 10) extending from their branch segments 18*a*, and the anchors 10 and 10*a* are arrayed in an alternating fashion with a column of modified anchors 10*a* between columns of anchors 10. This system 410 provides substantially the same arrangement as the first system 210, except with fewer extension segments, though at the expense of having two different anchors designs/parts to complete the anchoring system 410.

FIG. 16 shows a fourth system 510 of modified/alternative anchors 10*b* of a fourth example embodiment mounted to a vessel shell in a fourth arrangement and ready for application of the refractory. This fourth system 510 is substantially similar to the third system 410, with the anchors 10*b* arranged in an ordered array to cooperatively define some or all substantially hexagonal cells 550 in a tessellated pattern, except as noted herein.

In this system 510, the modified anchors 10*b* include the extension segments 24*b* on two diagonally opposite (catercorner) branch segments 18*b* and do not include the extension segments on the other two diagonally opposite branch segments 18*b*. This system 510 provides substantially the same arrangement as the third system 410, except with only one anchor design/part needed to complete the anchoring system 510.

FIG. 17 shows a fifth system 610 of modified/alternative anchors 10*c* of a fifth example embodiment mounted to a vessel shell in a fifth arrangement and ready for application of the refractory. This fifth system 610 is substantially similar to the fourth system 510, with the anchors 10*c* arranged in an ordered array to cooperatively define some or all substantially hexagonal cells 650 in a tessellated pattern, except as noted herein.

In this system 610, the modified anchors 10*c* include the extension segments 24*c* on two diagonally opposite (catercorner) branch segments 18*c* and do not include the extension segments on the other two diagonally opposite branch segments, as in the fourth system 510, and further the branch segments 18*c* without extension segments are shorter than those with them, so the extension segments of adjacent anchors 10*c* can be aligned in the manner depicted. This system 610 provides substantially the same arrangement as the fourth system 510, except with the anchors 10*c* arranged to form a regular hexagonal shape.

Figure 18:
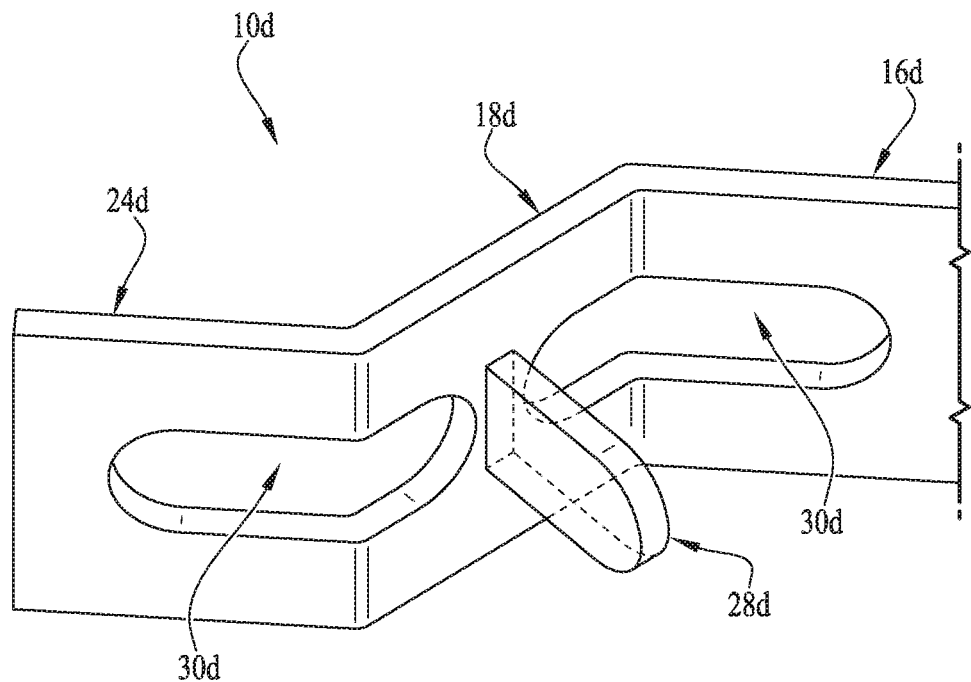
FIG. 18 is a perspective view of a portion of a refractory anchor according to a sixth example embodiment.
Figure 19:
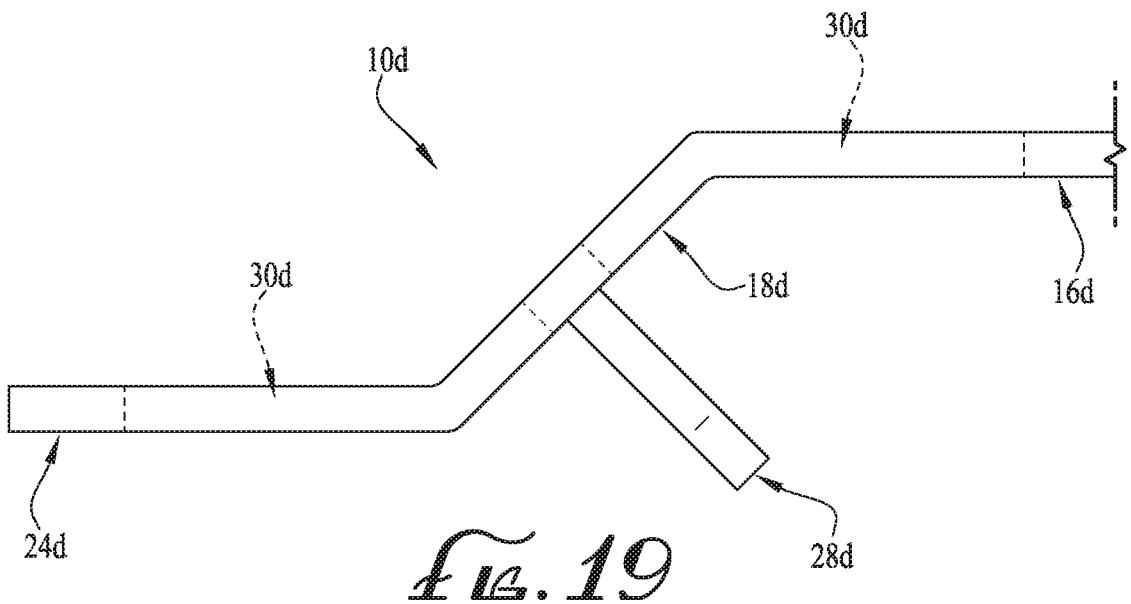
FIG. 19 is a top view of the refractory anchor portion of FIG. 18.

FIGS. 18-19 show a portion of a modified/alternative anchor 10*d* of a sixth example embodiment. The anchor 10*d* is substantially similar to those of the previously described embodiments, except as noted herein.

In this anchor 10*d*, the body includes voids 30*d* extending continuously through the central segment 16*d* and the branch segments 18*d*, in addition to the voids extending continuously through the branch segments 18*d* and the extension segments 24*d*, and the underbody gaps (at the bottom of the central and branch segments) are eliminated (as depicted) or reduced/minimized. As such, the anchor 10*d* has refractory flow passageways extending through and along the central, branch, and extension segments 16*d*, 18*d*, and 24*d* in a continuous manner except where the reinforcement segments 28*d* interrupt them (and adjoin two of the void ends).

Figure 20:
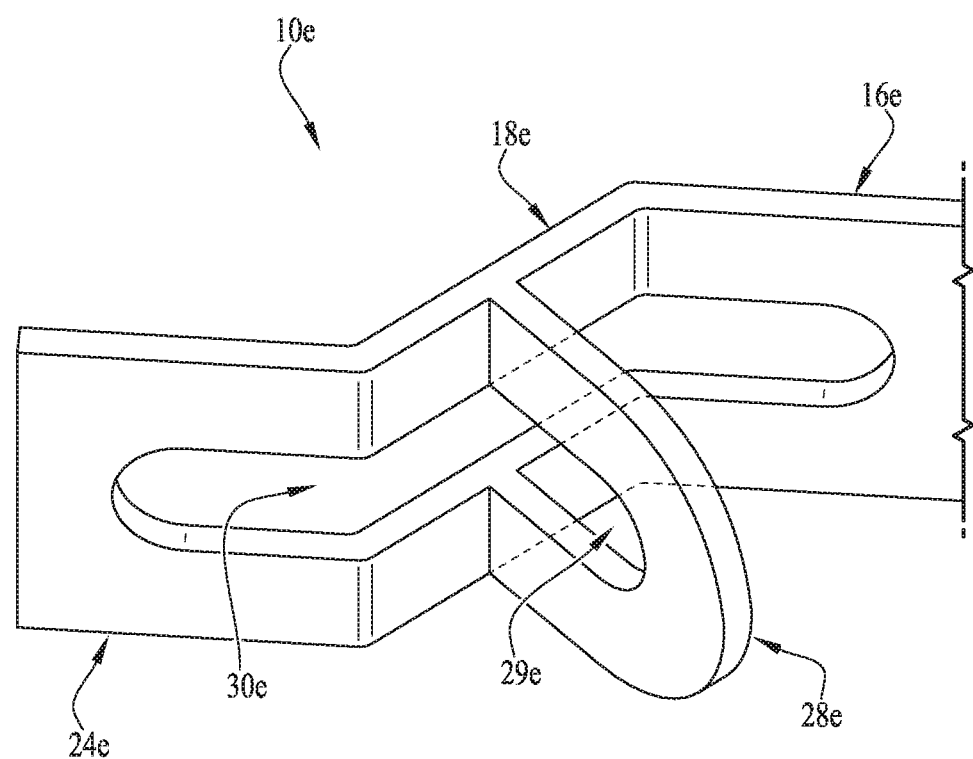
FIG. 20 is a perspective view of a portion of a refractory anchor according to a seventh example embodiment.

FIG. 20 shows a portion of a modified/alternative anchor 10*e* of a seventh example embodiment. The anchor 10*e* is substantially similar to that of the sixth embodiment, except as noted herein.

In this anchor 10*e*, the body includes voids 30*e* extending continuously through and along the central, branch, and extension segments 16*e*, 18*e*, and 24*e*, the reinforcement segments 28*e* have voids 29*e* that at least partially align and communicate with the body voids 30*e* (so there is not mechanical interference (obstruction or interruption) between them), and the underbody gaps (at the bottom of the central and branch segments) are eliminated (as depicted) or reduced/minimized. As such, the anchor 10*e* has a refractory flow passageway extending through and along the central, branch, and extension segments 16*e*, 18*e*, and 24*e* in a continuous manner, without interruption by the reinforcement segments 28*e* because of their voids 29*e*, which provide an additional flow passageway for additional refractory flow-through and retention.

In another aspect, the invention relates to a method of protecting thermal vessels with refractory linings by installing systems of refractory anchoring devices having unenclosed semi-polygonal openings to form anchor systems having polygonal cells for retaining the refractory. The method can include installing a number of the full-unit anchors 10, the half-unit anchors 110, and/or any of the other anchors 10*a-e* disclosed herein having unenclosed semi-hexagonal openings, and in some embodiments can additionally include installing other refractory anchors having unenclosed openings with other semi-polygonal shapes.

For example, when using the anchors 10, the method includes individually positioning each of the anchors 10 relative to the vessel shell and individually mounting them in place so that the semi-hexagonal openings 22 of adjacent anchoring devices 10 cooperate to form an ordered array/system 210 of generally hexagonal-shaped cells 250. In some embodiments, the refractory anchoring devices 10 include a single stud-welding stud 38 and the mounting process includes stud-welding the anchor devices 10 in place. The method contributes to providing the advantages of the anchors and anchor systems as described herein. The refractory can then be installed into the generally hexagonal cells 250 to complete the refractory lining process for the thermal vessel.

It is to be understood that this invention is not limited to the specific devices, methods, conditions, and/or parameters described and/or shown herein, and that the terminology used herein is for the purpose of describing particular embodiments by way of example only. Thus, the terminology is intended to be broadly construed and is not intended to be unnecessarily limiting of the claimed invention. For example, as used in the specification including the appended claims, the singular forms "a," "an," and "one" include the plural, the term "or" means "and/or," and reference to a particular numerical value includes at least that particular value, unless the context clearly dictates otherwise. In addition, any methods described herein are not intended to be limited to the specific sequence of steps described but can be carried out in other sequences, unless expressly stated otherwise herein.

While the invention has been shown and described in exemplary forms, it will be apparent to those skilled in the art that many modifications, additions, and deletions can be made therein without departing from the spirit and scope of the invention as defined by the following claims.

What is claimed is:

1. An anchoring device for a refractory material for lining a thermal vessel, the anchoring device comprising:
   a main body having the shape of two "Y"s arranged end-to-end and including a central segment, four branch segments extending from the central segment with a first pair of the branch segments extending from a first part of the central segment and with a second opposite pair of the branch segments extending from a second part of the central segment that is spaced apart from the first part, and four extension segments with each one extending from a respective one of the four branch segments,
   wherein the four branch segments are each angled with respect to the central segment at a first obtuse angle and the four extension segments are each angled relative to their respective branch segments at a second obtuse angle to form four unenclosed openings between them including two opposite central openings and two opposite end openings, wherein the four unenclosed openings are each semi-hexagonal in shape,
   wherein the main body further includes four reinforcement segments with each one extending into a respective one of the four unenclosed cell openings so that each of the four unenclosed cell openings has a respective reinforcement segment extending into it,
   wherein the main body further defines at least one body void that extends through and along at least one of the extension segments and the adjacent angled branch segment, and wherein the body void allows the refractory material to flow through the anchor main body when the anchor is mounted to the vessel and the refractory material is being installed, and
   wherein the main body further has at least one bottom surface that defines a base portion on one of the extension segments and an elevated portion on the central segment and elevated relative to the base portion to form an underbody gap between the main body bottom surface and the vessel, wherein the underbody gap allows the refractory material to flow under the anchor when the anchor is mounted to the vessel and the refractory material is being installed;
   a mounting element adapted to mount the main body to the thermal vessel; wherein the main body and the mounting element are made of a single component piece of a metal material that is formed by casting into a one-piece part, wherein the anchoring device includes no clinching mechanisms to fasten multiple parts together.

2. The anchoring device of claim 1, wherein the thermal vessel is of a type used in an oil refinery, another petrochemical-process facility, a chemical-process facility, a chemical-manufacturing plant, a cement plant, or another industrial facility for performing an industrial process in a high-temperature and caustic environment, and wherein the refractory material includes concrete, plastics, ceramics, another conventional refractory, or a combination thereof.

3. The anchoring device of claim 1, wherein each reinforcement segment extends from a respective one of the four branch segments, wherein the reinforcement segments are in addition to the branch segments and the extension segments, and do not define any portion of the four unenclosed openings.

4. The anchoring device of claim 1, wherein the main body bottom surface further defines a transition portion extending between the base and elevated portions.

5. The anchoring device of claim 4, wherein the transition portion is on the respective branch segment and is ramped upwardly from the extension segment toward the central segment.

6. The anchoring device of claim 1, wherein the at least one body void comprises four body voids with each body void extending through a respective one of the extension segments and the adjacent branch segment so that the body voids extend continuously through and along the angles between the respective extension and branch segments.

7. The anchoring device of claim 1, wherein ends of the body void and the underbody gap laterally overlap or are in vertical alignment.

8. The anchoring device of claim 1, wherein the obtuse angle between each extension segment and the respective branch segment is the same as the obtuse angle between each branch segment and the central segment, so that the extension segments are parallel to the central segment, and so that all four of the unenclosed openings have a same semi-hexagonal shape.

9. The anchoring device of claim 1, wherein each of the branch segments has a length that is substantially the same as a length of the central segment, and each of the extension segments has a length that is about half the length of the central and branch segments, wherein each of the four unenclosed cell openings has a same semi-hexagonal area.

10. The anchoring device of claim 1, wherein the mounting element includes a stud-welding stud defining a recess for receiving a pilot interface element, wherein the stud extends from the central segment of the anchor main body.

11. A system of a plurality of the anchoring devices of claim 1, wherein the anchoring devices are arranged in an ordered array of rows and columns to cooperatively define an ordered array of substantially hexagonal cells in a tessellated pattern.

12. A method of protecting a thermal vessel, comprising installing the anchoring system and the refractory material of claim 11.

13. An anchoring device for a refractory material for lining a thermal vessel, the anchoring device comprising:
   a main body having the shape of two "Y"s arranged end-to-end and including a central segment, four branch segments extending from the central segment with a first pair of the branch segments extending from a first part of the central segment and with a second opposite pair of the branch segments extending from a second part of the central segment that is spaced apart from the first part, and four extension segments with each one extending from a respective one of the four branch segments,
   wherein the four branch segments are each angled with respect to the central segment at a first obtuse angle and the four extension segments are each angled relative to their respective branch segments at a second obtuse angle to form four unenclosed openings between them including two opposite central openings and two opposite end openings, wherein the four unenclosed openings are each semi-hexagonal in shape, wherein the main body further includes four reinforcement segments with each one extending into a respective one of the four unenclosed cell openings so that each of the four unenclosed cell openings has a respective reinforcement segment extending into it, wherein the main body further defines four body voids that each extend continuously through at least one of the extension segments and the adjacent angled branch segment, wherein the body voids allow the refractory material to flow through the anchor main body when the anchor is mounted to the vessel and the refractory material is being installed, and wherein the main body further has at least one bottom surface that defines a base portion on one of the extension segments and an elevated portion on the central segment and elevated relative to the base portion to form an underbody gap between the main body bottom surface and the vessel, wherein the underbody gap allows the refractory material to flow under the anchor when the anchor is mounted to the vessel and the refractory material is being installed;

a mounting element adapted to mount the main body to the thermal vessel, wherein the mounting element includes a stud-welding stud defining a recess for receiving a pilot interface element, wherein the stud extends from the central segment of the anchor main body; wherein the main body and the mounting element are made of a single component piece of a metal material that is formed by casting into a one-piece part, wherein the anchoring device includes no clinching mechanisms to fasten multiple parts together.

14. The anchoring device of claim 13, wherein the thermal vessel is of a type used in an oil refinery, another petro-chemical-process facility, a chemical-process facility, a chemical-manufacturing plant, a cement plant, or another industrial facility for performing an industrial process in a high-temperature and caustic environment, and wherein the refractory material includes concrete, plastics, ceramics, another conventional refractory, or a combination thereof.

15. The anchoring device of claim 13, wherein each reinforcement segment extends from a respective one of the four branch segments, wherein the reinforcement segments are in addition to the branch segments and the extension segments, and do not define any portion of the four unenclosed openings.

16. The anchoring device of claim 13, wherein the main body bottom surface further defines a transition portion extending between the base and elevated portions, wherein the transition portion is on the respective branch segment and is ramped upwardly from the extension segment toward the central segment, and wherein ends of the body void and the underbody gap laterally overlap or are in vertical alignment.

17. The anchoring device of claim 13, wherein the obtuse angle between each extension segment and the respective branch segment is the same as the obtuse angle between each branch segment and the central segment, so that the extension segments are parallel to the central segment, and so that all four of the unenclosed openings have a same semi-hexagonal shape, and wherein each of the branch segments has a length that is substantially the same as a length of the central segment, and each of the extension segments has a length that is about half the length of the central and branch segments, wherein each of the four unenclosed cell openings has a same semi-hexagonal area.

18. A method of protecting a thermal vessel, comprising installing a plurality of the anchoring devices of claim 13 in an ordered array of rows and columns to cooperatively define an ordered array of substantially hexagonal cells in a tessellated pattern.

* * * * *